(12) United States Patent
Khalil et al.

(10) Patent No.: US 6,662,030 B2
(45) Date of Patent: Dec. 9, 2003

(54) NON-INVASIVE SENSOR HAVING CONTROLLABLE TEMPERATURE FEATURE

(75) Inventors: Omar S. Khalil, Libertyville, IL (US);
Frits F. M. de Mul, Almelo (NL);
Charles F. Hanna, Libertyville, IL (US); Arnold F. Stalder, Kenosha, WI (US); Shu-jen Yeh, Grayslake, IL (US); Xiaomao Wu, Gurnee, IL (US); Michael G. Lowery, Wildwood, IL (US); Johannes S. Kanger, Enschede (NL); René A. Bolt, Enschede (NL)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/080,470

(22) Filed: May 18, 1998

(65) Prior Publication Data

US 2002/0026106 A1 Feb. 28, 2002

(51) Int. Cl.[7] ................................................. A61B 5/00
(52) U.S. Cl. ....................... 600/316; 600/310; 600/322; 600/473; 600/476
(58) Field of Search ............................... 600/310, 322, 600/323, 334, 316, 473, 476

(56) References Cited

U.S. PATENT DOCUMENTS

| 3,628,525 A | 12/1971 | Polanyi et al. |
| 3,638,640 A | 2/1972 | Shaw |
| 4,223,680 A | 9/1980 | Jobsis |

(List continued on next page.)

FOREIGN PATENT DOCUMENTS

| DE | 4242083 | 6/1994 |
| DE | 44 17 639 | 11/1995 |
| DE | 196 34 152 | 3/1998 |

(List continued on next page.)

OTHER PUBLICATIONS

Applied Optics, vol. 31, No. 10, Apr. 1, 1992.
Kienle et al. "Spatially resolved absolute diffuse reflectance measurements for noninvasive determination of the optical scattering and absorption coefficients of biological tissue", Applied Optics, vol. 35, No. 13, May 1, 1996, pp. 2304–2314.

(List continued on next page.)

Primary Examiner—Eric F. Winakur
(74) Attorney, Agent, or Firm—David L. Weinstein

(57) ABSTRACT

Devices and methods for non-invasively measuring at least one parameter of a sample, such as the presence or concentration of an analyte, in a body part wherein the temperature is controlled. The present invention measures light that is reflected, scattered, absorbed, or emitted by the sample from an average sampling depth, $d_{av}$, that is confined within a temperature controlled region in the tissue. This average sampling depth is preferably less than 2 mm, and more preferably less than 1 mm. Confining the sampling depth into the tissue is achieved by appropriate selection of the separation between the source and the detector and the illumination wavelengths. In another aspect, the invention involves a method and apparatus for non-invasively measuring at least one parameter of a body part with temperature stepping. In another aspect, the invention involves a method and apparatus for non-invasively measuring at least one parameter of a body part with temperature modulation. In another aspect, the invention provides an improved method of measuring at least one parameter of a tissue sample comprising the steps of:

(a) lowering the temperature of said tissue sample to a temperature that is lower than the normal physiological temperature of the body; and (b) determining at least one optical property of said tissue sample.

44 Claims, 9 Drawing Sheets

U.S. PATENT DOCUMENTS

| | | | |
|---|---|---|---|
| 4,259,963 A | 4/1981 | Huch | |
| 4,432,365 A | 2/1984 | Leist | |
| 4,655,225 A | 4/1987 | Dahne et al. | |
| 4,882,492 A | 11/1989 | Schlager | |
| 4,890,619 A | 1/1990 | Hatschek | |
| 4,926,867 A | 5/1990 | Kanda et al. | |
| 4,975,581 A | 12/1990 | Robinson et al. | |
| 5,007,423 A | 4/1991 | Branstetter et al. | |
| 5,057,695 A | 10/1991 | Hirao et al. | |
| 5,086,229 A | 2/1992 | Rosenthal et al. | |
| 5,115,133 A | 5/1992 | Knudson | |
| 5,122,974 A | 6/1992 | Chance | |
| 5,131,391 A | 7/1992 | Sakai et al. | |
| 5,148,082 A | 9/1992 | Itou et al. | |
| 5,187,672 A | 2/1993 | Chance et al. | |
| 5,209,231 A | 5/1993 | Cote et al. | |
| 5,218,207 A | 6/1993 | Rosenthal | |
| 5,237,178 A | 8/1993 | Rosenthal | |
| 5,277,181 A | 1/1994 | Mendelson et al. | |
| 5,284,139 A | 2/1994 | Khalil et al. | |
| 5,297,548 A | 3/1994 | Pologe | |
| 5,313,941 A | 5/1994 | Braig et al. | |
| 5,321,265 A | 6/1994 | Block | |
| 5,324,979 A | 6/1994 | Rosenthal | |
| 5,337,745 A | 8/1994 | Benaron | |
| 5,348,002 A | 9/1994 | Caro | |
| 5,348,003 A | 9/1994 | Caro | |
| 5,361,758 A | 11/1994 | Hall et al. | |
| 5,362,966 A | 11/1994 | Rosenthal et al. | |
| 5,372,136 A | 12/1994 | Steuer et al. | |
| 5,379,764 A | 1/1995 | Barnes et al. | |
| 5,383,452 A | 1/1995 | Buchert | |
| 5,402,778 A | 4/1995 | Chance | |
| 5,452,716 A | 9/1995 | Clift | |
| 5,481,113 A | 1/1996 | Dou et al. | |
| 5,492,118 A | 2/1996 | Gratton et al. | |
| 5,492,769 A | 2/1996 | Pryor et al. | |
| 5,497,769 A | 3/1996 | Gratton et al. | |
| 5,499,627 A | 3/1996 | Steuer et al. | |
| 5,515,847 A | 5/1996 | Braig et al. | |
| 5,533,509 A | 7/1996 | Koashi et al. | |
| 5,551,422 A | 9/1996 | Simonsen et al. | |
| 5,553,615 A | 9/1996 | Carim et al. | |
| 5,553,616 A | 9/1996 | Ham et al. | |
| 5,596,987 A | 1/1997 | Chance | |
| 5,665,530 A | 9/1997 | Oyamada et al. | |
| 5,672,875 A | 9/1997 | Block et al. | |
| 5,676,143 A | 10/1997 | Simonsen et al. | |
| 5,692,503 A | 12/1997 | Kuenstner | |
| 5,720,284 A | 2/1998 | Aoyagi et al. | |
| 5,725,480 A | 3/1998 | Oosta et al. | |
| 5,755,226 A | 5/1998 | Carim et al. | |
| 5,770,454 A | 6/1998 | Essenpreis et al. | |
| 5,782,755 A | 7/1998 | Chance et al. | |
| 5,823,951 A | 10/1998 | Messerschmidt | |
| 5,873,821 A | 2/1999 | Chance et al. | |
| 5,935,062 A | 8/1999 | Messerschmidt et al. | |
| 5,978,691 A * | 11/1999 | Mills | 600/334 |
| 6,016,435 A | 1/2000 | Maruo et al. | |

FOREIGN PATENT DOCUMENTS

| | | |
|---|---|---|
| EP | 0472216 | 2/1992 |
| EP | 0810429 | 12/1997 |
| WO | 9210131 | 6/1992 |
| WO | 9220273 | 11/1992 |
| WO | 9307801 | 4/1993 |
| WO | 9313706 | 7/1993 |
| WO | 9402837 | 2/1994 |
| WO | 9405984 | 3/1994 |
| WO | 9413199 | 6/1994 |
| WO | 95/20757 | 8/1995 |
| WO | 98/03847 | 1/1998 |
| WO | 99/55222 | 4/1999 |
| WO | 99/39631 | 8/1999 |
| WO | 9959464 | 11/1999 |

OTHER PUBLICATIONS

Wilson et al., "Progress Toward the Development of an Implantable Sensor for Glucose", Clinical Chemistry, vol. 38, No. 9, (1992) pp. 1613–1617.

Tooke et al., "Skin Microvascular Blood Flow Control in Long Duration Diabetics with and Without Complications", Diabetes Research, No. 5, (1987), pp. 189–192.

Qu et al. "Monte Carlo Modeling Studies of the Effect of Physiological Factors and other Analytes on the Determination of Glucose Concentration In Vivo By Near Infrared Optical Absorption and Scattering Measurements", Journal of Biomedical Optics, vol. 2, No. 3, Jul. 1997, pp. 319–325.

Robbins et al., Pathologic Basis of Disease, $3^{rd}$ Edition, "The Endocrine Pancreas", W.B. Saunders Company (1984), pp. 972–990.

Quan et al., "Glucose determination by a pulsed photoacoustic technique: an experimental study using a gelatin-based tissue phantom", Phys. Med. Biol., vol. 38 (1993), pp. 1911–1922.

R. Graaff, et al., "Reduced light–scattering properties for mixtures of spherical particles: a simple approximation derived from Mie calculations", Applied Optics, vol. 31, No. 10, Apr. 1, 1992, pp. 1370–1376.

Jobsis, "Noninvasive, Infrared Monitoring of Cerebral and Myocardial Oxygen Sufficiency and Circulatory Parameters", *Science*, vol. 198, 1977, pp. 1264–1267.

Gopinath, et al., "Near–infrared spectroscopic localization of intracranial hematomas", *Journal of Neurosurgery*, vol. 79, 1993, pp. 43–47.

Zhang, et al., "Investigation of Noninvasive in Vivo Blood Hematocrit Measurement Using NIR Reflectance Spectroscopy and Partial Least–Squares Regression", *Applied Spectroscopy*, vol. 54, No. 2, 2000, pp. 294–299.

Lin, et al., "Dynamics of tissue optics during laser heating of turbid media", *Applied Optics*, vol. 35, No. 19, 1996, pp. 3413–3420.

Laufer, et al., "Effect of temperature on the optical properties of ex vivo human dermis and subdermis", *Phys. Med. Biol.*, vol. 43, 1998, pp. 2479–2489.

Bruulsema, et al,. "Optical Properties of Phantoms and Tissue Measured in vivo from 0.9–1.3 $\mu$m using Spatially Resolved Diffuse Reflectance", *SPIE Proceedings*, vol. 2979, 1997, pp. 325–334.

T. Shiga, et al., "Study of an Algorithm Based on Model Experiments and Diffusion Theory for a Portable Tissue Oximeter", *Journal of Biomedical Optics*, vol. 2, No. 2, Apr. 1997, pp. 154–161.

Jacques, et al., "Monte Carlo Modeling of Light Transport in Tissue", *Optical–Thermal Response of Laser–Irradiated Tissue*, edited by A.J. Welch and M.J.C. van Gemert, Plenum Press, New York, 1995, pp. 73–100.

Wilson, "Measurement of Tissue Optical Properties: Methods and Theories", *Optical–Thermal Response of Laser–Irradiated Tissue*, edited by A.J. Welch and M.J.C. van Gemert, Plenum Press, New York, 1995, pp. 233–274.

Morris, et al., "Basic Examination of Blood", *Clinical Diagnosis and Management by Laboratory*, 1996, pp. 549–559.

Lin, et al., "Dynamics of tissue reflectance and transmittance during laser irradiation", *SPIE Proceedings*, vol. 2134A Laser–Tissue Interaction V, 1994, pp. 296–303.

Bruulsema, et al., "Correlation between blood glucose concentration in diabetics and noninvasively measured tissue optical scattering coefficient", Optics Letters, vol. 22, No. 3, 1997, pp. 190–192.

Heinemann, et al., "Non–invasive continuous glucose monitoring in Type I diabetic patients with optical glucose sensors", Diabetologia, vol. 41, 1998, pp. 848–854.

Marbach, et al., "Noninvasive Blood Glucose Assay by Near–Infrared Diffuse Reflectance Spectroscopy of the Human Inner Lip", Applied Spectroscopy, vol. 47, No. 7, 1993, pp. 875–881.

* cited by examiner

NON-INVASIVE SENSOR HAVING CONTROLLABLE TEMPERATURE FEATURE

BACKGROUND OF THE INVENTION

1. Field of the Invention

This invention relates to devices and methods for measuring the concentration of one or more analytes in a human body part. More specifically, this invention relates to devices and methods for the noninvasive determination of in vivo analyte concentrations under conditions of precise temperature control.

2. Discussion of the Art

Non-invasive optical monitoring of metabolites is an important tool for clinical diagnostics. The ability to determine an analyte, or a disease state, in a human subject without performing an invasive procedure, such as removing a sample of blood or a biopsy specimen, has several advantages. These advantages include ease of performing the test, reduced pain and discomfort, and decreased exposure to potential biohazards. The result will be increased frequency of testing, accurate monitoring and control, and improved patient care. Representative examples of non-invasive measurements include pulse oximetry for oxygen saturation (U.S. Pat. Nos. 3,638,640; 4,223,680; 5,007,423; 5,277,181; 5,297,548), laser Doppler flowmetry for diagnosis of circulation disorder (Toke et al, "Skin microvascular blood flow control in long duration diabetics with and without complication", Diabetes Research, Vol. 5, Pages 189–192, 1987), determination of tissue oxygenation (WO 92/20273), determination of hemoglobin (U.S. Pat. No. 5,720,284) and of hematocrit (U.S. Pat. Nos. 5,553,615; 5,372,136; 5,499,627; WO 93/13706).).

Measurements in the near-infrared spectral region are commonly proposed, or used, in prior art technologies. The 600–1100 nm region of the spectrum represents a window between the visible hemoglobin and melanin absorption bands and the infrared strong water absorption band. Light can penetrate deep enough in the skin to allow use in a spectral measurement or a therapeutic procedure.

Oximetry measurement is very important for critical patient care, especially after use of anesthesia. Oxygenation measurements of tissue are also important diagnostic tools for measuring oxygen content of the of the brain of the newborn during and after delivery and for sports medicine and tissue healing monitoring. Non-invasive determination of hemoglobin and hematocrit would offer a simple non-biohazardous painless procedure for use in blood donation centers, thereby increasing the number of donations by offering an alternative to the invasive procedure, which is inaccurate and could lead to rejection of a number of qualified donors. Hemoglobin and hematocrit values are useful for the diagnosis of anemia in infants and mothers, without the pain associated with pediatric blood sampling. Non-invasive determination of hemoglobin has been studied in the art as a method for localizing tumors and diagnosis of hematoma and internal bleeding. Non-invasive hematocrit measurements can yield important diagnostic information on patients with kidney failure before and during dialysis. There are more than 50 million dialysis procedures performed in the United Stated and close to 80 million procedures performed world-wide per year.

The most important potential advantage for non-invasive diagnostics possibly will for non-invasive diagnosis of diabetes. Diabetes mellitus is a chronic disorder of carbohydrate, fat, and protein metabolism characterized by an absolute or relative insulin deficiency, hyperglycemia, and glycosuria. At least two major variants of the disease have been identified. "Type I" accounts for about 10% of diabetics and is characterized by a severe insulin deficiency resulting from a loss of insulin-secreting beta cells in the pancreas. The remainder of diabetic patients suffer from "Type II", which is characterized by an impaired insulin response in the peripheral tissues (Robbins, S. L. et al., *Pathologic Basis of Disease,* 3rd Edition, W. B. Saunders Company, Philadelphia, 1984, p. 972). If uncontrolled, diabetes can result in a variety of adverse clinical manifestations, including retinopathy, atherosclerosis, microangiopathy, nephropathy, and neuropathy. In its advanced stages, diabetes can cause blindness, coma, and ultimately death.

The principal treatment for Type I diabetes is periodic insulin injection. Appropriate insulin administration can prevent, and even reverse, some of the adverse clinical outcomes for Type I diabetics. Frequent adjustments of the blood glucose level can be achieved either by discrete injections or, in severe cases, via an implanted insulin pump or artificial pancreas. The amount and frequency of insulin administration is determined by frequent or, preferably, continuous testing of the level of glucose in blood (i. e., blood glucose level).

Tight control of blood glucose in the "normal range", 60–120 mg/dL, is necessary for diabetics to avoid or reduce complications resulting from hypoglycemia and hyperglycemia. To achieve this level of control, the American Diabetes Association recommends that diabetics test their blood glucose five times per day. Thus, there is a need for accurate and frequent or, preferably, continuous glucose monitoring to combat the effects of diabetes.

Conventional blood glucose measurements in a hospital or physician's office rely on the withdrawal of a 5–10 mL blood sample from the patient for analysis. This method is slow and painful and cannot be used for continuous glucose monitoring. An additional problem for hospitals and physician offices is the disposal of testing elements that are contaminated by blood.

Implantable biosensors have also been proposed for glucose measurement. (G. S. Wilson, Y. Zhang, G. Reach, D. Moatti-Sirat, V. Poitout, D. R. Thevenot, F. Lemonnier, and J.-C. Klein, Clin. Chem. 38, 1613 (1992)). Biosensors are electrochemical devices having enzymes immobilized at the surface of an electrochemical transducer.

Portable, "minimally-invasive" testing systems are now commercially available. These systems require the patient to stick themselves to obtain a drop of blood which is then applied to a disposable test strip containing coated reagents or an electrochemical test element.

Although the portable instruments that read the strips are relatively inexpensive ($100–$200), the cumulative cost to diabetics for the disposable strips is considerable. Compliance is another major problem for minimally invasive techniques. Finger sticks are painful and can result in infections, scarring, and nerve damage in the finger. Disposal of potentially biohazardous test strips and lancets is yet another problem with these systems.

"Non-invasive" (alternatively referred to herein as "NI") glucose sensing techniques measure in-vivo glucose concentrations without collecting a blood sample. As defined herein, a "non-invasive" technique is one that can be used without removing a sample from, or without inserting any instrumentation into, the tissues. The concept involves irradiating a vascular region of the body with electromagnetic radiation and measuring the spectral information that results from one of four primary processes: reflection, absorption, scattering, and emission. The extent to which each of these processes occurs is dependent upon a variety of factors, including the wavelength and polarization state of the incident radiation and the glucose concentration in the body part. Glucose concentrations are determined from the spectral information by comparing the measured spectra to a calibration curve or by reference to a physical model of the tissue under examination. Various categories of non-invasive glucose measurement techniques will now be described.

NI techniques that utilize the absorption of infrared radiation can be divided into three distinct wavelength regimes: Near-infrared (NIR), Mid-infrared (MIR) and Far-infrared (FIR). As defined herein, NIR involves the wavelength range from about 600 nm to about 1200 nm, MIR involves the wavelength range from about 1200 nm to about 3000 nm and FIR involves the wavelength range from about 3000 nm to about 25000 nm. As defined herein, "infrared" (or IR) is taken to mean a range of wavelengths from about 600 nm to about 25000 nm.

U.S. Pat. Nos. 5,086,229; 5,324,979; and 5,237,178 describe non-invasive methods for measuring blood glucose level involving NIR radiation. In general, a blood-containing body part (e. g., a finger) is illuminated by one or more light sources, and the light that is transmitted through the body part is detected by one or more detectors. A glucose level is derived from a comparison to reference spectra for glucose and background interferants. The 600–1100 nm spectral region contains a portion of the hemoglobin and water absorption bands, which are several orders of magnitude more intense than glucose overtone absorption bands. Thus, errors in the measurement of hemoglobin absorption, water absorption, tissue scattering, and blood scattering will greatly affect the glucose signal measured in this spectral range. Determination of hemoglobin and study of the factors affecting the hemoglobin-related signal are important for the determination of glucose when spectral data generated in the NIR region are employed. Thus, in addition to the diagnostic value of hemoglobin and hematocrit determinations, these determinations are important for estimating the variability in non-invasive glucose measurements. The NIR spectral region has been used for determination of blood oxygen saturation, hemoglobin, hematocrit, and tissue fat content. It is also used for exciting and detecting compounds in photodynamic therapy.

The use of MIR radiation for NI glucose measurement has been described in U.S. Pat. Nos. 5,362,966; 5,237,178; 5,533,509; and 4,655,225. The principles of operation are similar to those described for NIR radiation, except that the penetration depth of the MIR radiation is less than that of NIR radiation. As a consequence, most measurements in this region have been performed using a backscattering geometry. As defined herein, a "backscattering geometry" describes a configuration wherein scattered radiation is collected on the same side of the sample as the entry point of the incident radiation. A "transmission geometry" describes a configuration wherein light is transmitted through the sample and collected on the side of the sample opposite to the entry point of the incident radiation. This spectral region is less useful for the determination of hemoglobin and hematocrit. However the 1300–1390 nm wavelength has been used as a reference and water absorption wavelength for hematocrit determination.

FIR measurements have been described in U.S. Pat. Nos. 5,313,941; 5,115,133; 5,481,113; 5,452,716; 5,515,847; 5,348,003; and DE4242083.

The photoacoustic effect results from the absorption of a pulse of optical energy by tissues of a test subject, which optical energy is rapidly converted into thermal energy. The subsequent thermal expansion generates an acoustic pressure wave, which is measured by an acoustic transducer. In addition to the absorption of light, the measured photoacoustic signal depends upon the speed of sound in the medium, the thermal expansion coefficient, and the specific heat of the medium.

Glucose measurements employing the photoacoustic effect have been described by Quan et al. (K. M. Quan, G. B. Christison, H. A. MacKenzie, P. Hodgson, Phys. Med. Biol., 38 (1993), pp. 1911–1922) and U.S. Pat. No. 5,348, 002.

Methods for the determination of glucose concentrations using changes in the polarization of light are described WO 92/10131, WO 93/07801, WO 94/02837, WO 94/05984, and WO 94/13199 and U.S. Pat. Nos. 4,882,492; 5,086,229; 5,209,231; 5,218,207; 5,321,265; 5,337,745; 5,361,758; and 5,383,452.

An electromagnetic wave incident on an isolated molecule with an electron cloud will cause the electrons to oscillate about their equilibrium positions, in synchrony with the applied wave. The resulting electronic oscillator instantaneously emits radiation (scatters) in all directions in a plane perpendicular to the oscillating electrons. Most of the scattered photons are elastically scattered, i. e., they have the same frequency as the incident radiation. A small fraction of the scattered light (less than one in a thousand incident photons) is inelastically (Raman) scattered. Unless otherwise indicated herein, "scattering" refers to elastic scattering.

Because of the multiple scattering effect of tissue, optical measurements, whether in transmission or reflectance, will contain tissue scattering information, as well as absorption information. Tissue scattering information includes cell size and cell shape, depth of layers and refractive index of intracellular fluids and extracellular fluids. Absorption information includes absorption by visible components, such as hemoglobin, melanin, and bilirubin, and the overtone absorption of water, glucose, lipids, and other metabolites.

Spatially resolved light scattering (SRLS) techniques are a subset of the elastic scattering methods previously described. As shown in FIG. 1, light is injected into the surface of a tissue sample, such as a body part, at an injection point. The diffusely reflected light, R, is measured at two or more detection points located on the sample surface (e. g., the skin) at different detector distances, r, from the injection point. The dependence of the intensity of the diffuse reflectance R as a function of the detector distance (r) is used to derive scattering and absorption coefficients of the tissue sample. These coefficients, in turn, are related to the concentration of analyte(s). SRLS techniques have been described U.S. Pat. Nos. 5,551,422; 5,676,143; 5,492,118; 5,057,695, European Patent Application EP 0810429, and in the journal literature (B. Chance, H. Liu, T. Kitai, Y. Zhang, Analytical Biochemistry, 227, 1995, pp. 351–362. H. Liu, B. Beauvoit, M. Kimura, B. Chance, Journal of Biomedical Optics, 1(2), April, 1996, pp. 200–211. J. Qu, B. Wilson, Journal of Biomedical Optics, 2(3), July 1997, pp. 319–325; A. Kienle, L. Lilge, M. Patterson, R. Hibst, R. Steiner, B. Wilson, Applied Optics, 35(13), May 1996, pp. 2304–2314.

Frequency-domain reflectance measurements use optical systems similar to those used for spatially resolved light scattering (R as a function of r), except that the light source and the detector are modulated at a high frequency (U.S. Pat.

Nos. 5,187,672; 5,122,974). The difference in phase angle and modulation between injected and reflected beam is used to calculate the reduced scattering coefficient and the absorption coefficient of the tissue or turbid medium. U.S. Pat. No. 5,492,769 describes frequency domain method and apparatus for the determination of a change in the concentration of an analyte, and U.S. Pat. No. 5,492,118 describes a method and apparatus for determination of the scattering coefficient of tissues.

U.S. Pat. No. 5,553,616 describes the use of Raman scattering with NIR excitation and an artificial neural network for measuring blood glucose level. Although glucose Raman bands are distinct from protein Raman bands, sensitivity of this method limits its applicability for in-vivo measurements. WO 92/10131 discusses the application of stimulated Raman spectroscopy for detecting the presence of glucose.

The NI techniques described above are painless, reagentless, and are expected to be less expensive than the finger stick approach over the long term use by a patient. NI techniques also eliminate the potentially biohazardous waste associated with invasive and minimally invasive measurements. However, NI methods have not yet achieved the level of accuracy and precision that is required for measuring physiologically relevant concentrations of glucose in-vivo.

A major challenge for all of the non-invasive techniques to date has been to collect spectral information with sufficiently high signal-to-noise ratios to discriminate weak glucose signals from the background noise. In the ideal case, a non-invasive sensor would be highly sensitive for the parameter of interest (e. g., glucose concentration) while remaining insensitive to interfering analytes or physiological parameters. In practice, all of the non-invasive measurement techniques described in the prior art are sensitive to one or more interfering "physiological" or "spectral" variables.

As used herein, the expression "physiological variables" describes physiological parameters, such as temperature, that can adversely affect the sensitivity or selectivity of a non-invasive measurement. As used herein, the expression "spectral variables" describes spectral features that arise either from poorly resolved analyte bands or from other interfering components in the sample. Several significant sources of spectral interference for the NI determination of glucose in biological samples are water, hemoglobin, albumin, cholesterol, urea, etc. Other tissue constituents that are present at lower concentrations or have lower absorption or scattering cross-sections may also contribute to an overall background signal that is difficult to separate.

Physiological and spectral variables can introduce unwanted noise, or worse, completely overwhelm the measured signals of interest (e. g., those related to glucose concentration). It is difficult to eliminate these interferences because they may exhibit one or more of the following properties:

(a) they may contribute nonlinearly to the measured signal,
(b) they may vary with spatial location within the sample,
(c) they may vary over time, or
(d) they may vary from sample to sample.

Co-pending U.S. application Ser. No. 08/982,939, filed Dec. 2, 1997, assigned to the assignee of this application, describes a multiplex sensor that combines at least two NI techniques selected from those described above in order to compensate for the effects of spectral and physiological variables. A description of prior art measurements in which tissue temperature is controlled is provided below.

U.S. Pat. Nos. 3,628,525; 4,259,963; 4,432,365; 4,890,619; 4,926,867; 5,131,391, and European Patent Application EP 0472216 describe oximetry probes with heating elements that are placed against a body part. These devices enhance sensitivity of the oximeter by elevating local tissue perfusion rates, thereby increasing hemoglobin concentrations. U.S. Pat. No. 5,148,082 describes a method for increasing the blood flow in a patient's tissue, during a photoplethsmography measurement, by warming the tissue with heat generated by a semiconductor device mounted in a sensor. The heating element comprises a less efficient photodiode that acts as a heat source and as a light source.

U.S. Pat. No. 5,551,422 describes a glucose sensor that is "brought to a specified temperature preferably somewhat above normal body temperature (above 37° C.) with a thermostatically controlled heating system". Unlike the oximetry sensors, simply increasing tissue perfusion without controlling it is contraindicated for glucose measurements, because hemoglobin interferes with glucose measurement. This patent also fails to account for large variations in scattering intensity that result from the temperature gradient between the skin surface and the interior of the body part. As will be described more thoroughly below, the smallest devices disclosed in that patent have an average sampling depth of 1.7 mm. Depths and lateral distances of several millimeters are sampled at the longest spacings between source and detector taught in that patent. As shown in FIG. 1 and as defined herein, the average sampling depth, $d_{av}$, is the average penetration depth along an axis normal to the tissue surface that is sampled in a given NI measurement. A thermal model of the human forearm, shown in FIGS. 6–8, suggests that, depending on the ambient temperature, the temperature of the tissue at a depth of 1.7 mm could be as much as 0.5° C. warmer than that of the skin surface. According to Wilson et al., (J. Qu, B. Wilson, Journal of Biomedical Optics, 2(3), July 1997, pp. 319–325), the change in scattering expected for a 0.5° C. change in temperature is equivalent to a 5 mM (90 mg/dL) change in glucose concentration. Thus, the scattering variability due to the temperature gradient probed by U.S. Pat. No. 5,551,422 is as large as the signal expected for normal physiological glucose levels.

Although a variety of spectroscopic techniques are disclosed in the prior art, there is still no commercially available device that provides noninvasive glucose measurements with an accuracy that is comparable to invasive methods. All of the prior art methods respond to glucose concentrations, but they are also sensitive to physiological and spectral variables. As a result, current approaches to non-invasive glucose testing have not achieved acceptable precision and accuracy.

Thus, there is a continuing need for improved NI instruments and methods that are unaffected by variations in tissue such as temperature and perfusion. There is also a need for improved NI instruments and methods that will provide essentially the same accuracy as conventional, invasive blood glucose tests. There is also a need for low-cost, reagent-free, painless, and environmentally friendly instruments and methods for measuring blood glucose levels in diabetic or hypoglycemic patients.

SUMMARY OF THE INVENTION

In one aspect, the present invention involves devices and methods for non-invasively measuring at least one parameter of a sample, such as the presence or concentration of an analyte, in a body part wherein the temperature is controlled. As will be described more fully below, the present invention measures light that is reflected, scattered, absorbed, or emitted by the sample from an average sampling depth, $d_{av}$, that is confined within a temperature controlled region in the tissue. This average sampling depth is preferably less than 2 mm, and more preferably less than 1 mm. Confining the sampling depth into the tissue is achieved by appropriate selection of the separation between the light introduction site and the light collection site and the illumination wavelengths.

Confining the sampling depth provides several advantages. First, the entire signal is acquired from a region of tissue having a substantially uniform temperature. As defined herein, a "substantially uniform tissue temperature" means that the temperature of the tissue varies by no more than ±0.20° C., preferably no more than ±0.1° C. Secondly, the sampled tissue region is more homogeneous than the tissue regions sampled by the devices of the prior art. As a result, physiological and spectral interferences are controlled so that their contributions may be separated, quantified, and removed from the signals of interest.

In the present invention, the area of the skin of the body part where temperature is controlled is larger than the optical sampling area. A preferred ratio of the area of controlled temperature (surface area of the temperature controlled body interface) to the optical sampling area (surface area of the optical probe) is greater than 2:1, preferably greater than 5:1.

In another aspect, the present invention involves a method and apparatus for non-invasively measuring at least one parameter of a body part with temperature stepping. As defined herein, "temperature stepping" comprises changing the temperature of a tissue sample between at least two different predefined temperatures. Non-invasive measurements are performed at each of the two or more different temperatures in order to remove the effects of temperature fluctuations on the measurement.

In another aspect, the present invention involves a method and apparatus for non-invasively measuring at least one parameter of a body part with temperature modulation. As used herein, temperature modulation consists of cycling the temperature (changing the temperature repeatedly) between at least two different predefined temperatures. Non-invasive measurements are performed at each of the two or more different temperatures in order to eliminate the effects of temperature fluctuations on the measurement.

In another aspect, the present invention provides an improved method of measuring at least one parameter of a tissue sample comprising the steps of:
 (a) lowering the temperature of said tissue sample to a temperature that is lower than the normal physiological temperature of the body; and
 (b) determining at least one optical property of said tissue sample.

In another aspect, the present invention provides a method of measuring at least one parameter of a tissue sample comprising the steps of:
 (a) stepping the temperature of said tissue sample between at least two different temperatures;
 (b) measuring said at least one optical property of the tissue sample as a function of temperature;
 (c) computing the change in the at least one optical property as a function of change in temperature; and
 (d) correlating the at least one parameter of the tissue sample with the functional dependence of the at least one optical property on temperature.

The present invention is particularly advantageous for biological samples where multiple interfering analytes or physiological variables can affect the measurement. Non-invasive measurements may be made on a body part of a patient, e. g., a finger, earlobe, lip, toe, skin fold, or bridge of the nose.

The invention offers several advantages over the prior art. At small separations of light introduction site from light collection site, light samples penetrate the tissue to a lower depth, where smaller temperature gradients are encountered, than to deeper regions of the tissue. In addition, better temperature control can be achieved at lower depths of penetration in the sampled region. If the separation of light introduction site from light collection site varies over large distances (e. g., 0.5 cm–7 cm), light from the light introduction site and collected light propagates through the epidermis, the dermis, as well as deeper regions of tissue, including the subcutis (which has higher fatty adipose tissue content) and underlying muscle structures. These layers provide sources of variability in measurements because of the difference in cell size, cell packing, blood content, as well as thermal properties.

In addition, for tissue that is heterogeneous along dimensions parallel to the skin surface (x and y), there is lower likelihood of photons encountering tissue components that will cause anomalies in the scattering measurements. It is also possible to perform measurements on a small localized area of the skin with a probe design having a closely spaced light introduction site and light collection site than with a light introduction site that is located a great distance from the light collection site. Thus, it is possible to detect blood vessels and hair fibers and determine their effect on the signal.

Probes having large separations of light introduction site from light collection site require the use of a large body mass, such as the muscle of the arm, thigh, or the abdomen. Accordingly, the body site locations where such a probe can be used on are limited, and substantial disrobing and inconvenience for the user is required. Thus, another advantage of the probe design of the present invention is that probes of 5 mm or less can be used, particularly with small body parts, such as ear lobes and fingers. However, probes of 5 mm or less can also be used with larger body parts, such as the forearm, thigh, or abdomen.

Another advantage of a small separation between light introduction site and light collection site is the higher signal to noise ratio obtainable at small separations due to increases in the amount of light reaching the light collection site. Thus simpler, inexpensive, rugged components, such as light emitting diodes, small flash lamps, and incandescent lamps, can be used as light sources, and commercially available inexpensive photodiodes can be used as detectors. Probes having a large separation between light introduction site and light collection site use laser diodes and photomultiplier tubes, because weaker signals are generated.

In addition to convenience and cost advantages, other engineering design considerations favor the probe design of the present invention. It is preferred to generate a constant temperature using standard Peltier cooler elements that are approximately 1 cm squares. In order to obtain an aspect ratio of 5/1, probes of 2 mm or less are desirable, especially for use with small body parts, such as ear lobes and fingers. Larger thermoelectric cooling and heating elements may be employed at a cost of higher power consumption and greater heat dissipation.

Prior art measurements that use separations of light collection site and light introduction site in excess of 3 mm result in the phase and polarization of the incident light that are randomized. However, in the present invention, the preferred separations are less than 2 mm, and polarization and interference effects can be measured. The use of polarizers and polarization conserving fibers can reveal some internal sample properties. In addition, temperature effects on transmission of polarized light through tissue can be studied with the apparatus of the present invention.

DETAILED DESCRIPTION

Figure 1:
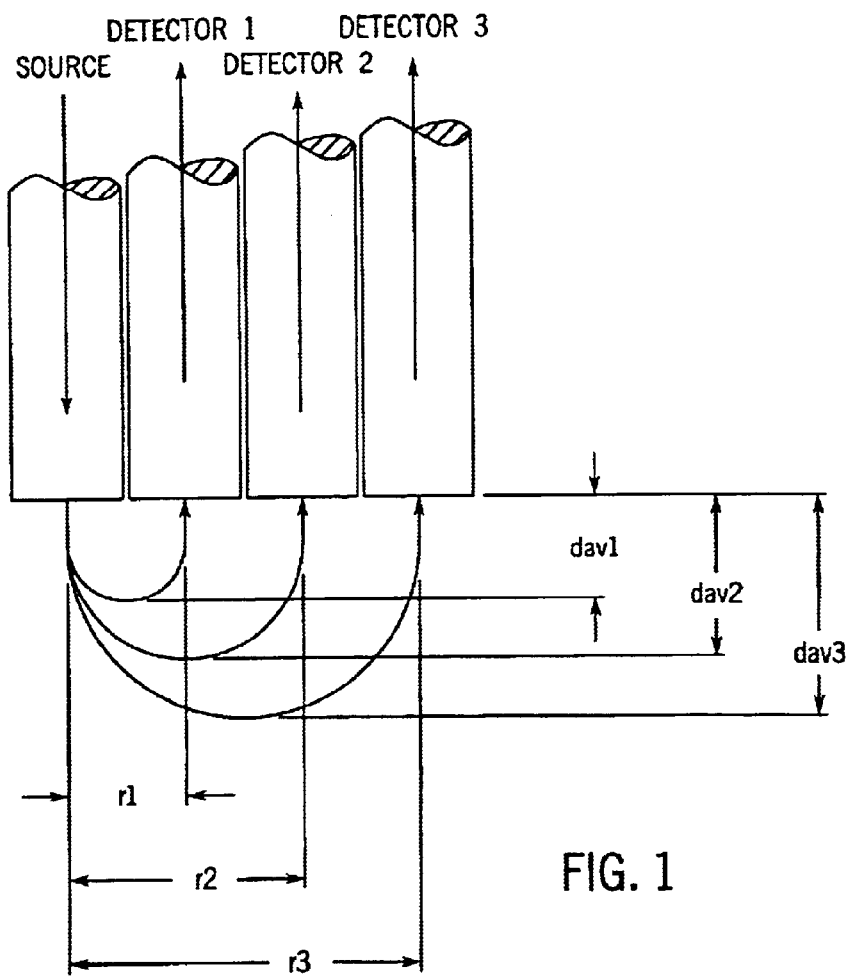
FIG. 1 is a schematic diagram of the average sampling depth, $d_{av}$, for a given spatially-resolved light scattering measurement.

As used herein, the expression "tissue optics" refers to the study of light propagation in biological tissues. The expression "optical properties" refers to the absorption, scattering, and depolarization properties of the tissues. The expression "scattering media" refers to media that both scatters light and absorbs light. The expression "absorption coefficient, $\mu_a$" refers to the probability of light absorption per unit path length. The expression "scattering coefficient, $\mu_s$" refers to the probability of light scattering per unit path length. The expression "isotropy factor, g" refers to the average cosine of the scattering angle for a multiply scattering photon. The expression "reduced scattering coefficient $\mu_s'$" refers to the probability of equivalently isotropic scattering per unit path length. The reduced scattering coefficient is related to the scattering coefficient $\mu_s$ and the anisotropy factor g by the relationship $\mu_s'=(1-g)\mu_s$. The expression "transport optical mean free path" refers to the mean path length between photon-medium interaction, which can be either absorption or scattering; mean free path=$(1/(\mu_a+\mu_s'))$. The expression "effective scattering coefficient" refers to the transport attenuation coefficient, $\mu_{eff}=\sqrt{3}\,\mu_a(\mu_a+\mu_s')$. The expression "penetration depth, $\delta$" refers to the speed of light intensity decay in turbid media. Penetration depth is determined by both the absorption and scattering coefficient, $\delta=1/\mu_{eff}$. The expression "Monte Carlo simulations" refers to a statistical method that can be used to trace photon propagation in turbid media. The expression "diffuse reflectance" refers to a process by which light reflected from a boundary of a sample is measured at all angles and over an area wider than the beam diameter. The expressions "spatially resolved scattering" or "spatially resolved reflectance" refers to a process by which light injected at certain point on a boundary of the sample is detected at several light measurement points and at a predetermined spacing from the light injection point. Alternatively, it can be defined as the light detected at a given point on the sample boundary as a result of injecting light at discrete points located on the same boundary at predetermined separation distances. The expression "frequency domain measurement" refers to a measurement of light involving the phase angle and/or the amplitude change of a modulated light beam, at a given separation of source and detector, as the beam transverses a scattering medium.

In "warm-blooded" animals, such as birds and mammals, a group of reflex responses operate to maintain body temperature within a narrow range in spite of wide fluctuations in environmental temperature. In humans, the normal value for the oral temperature is 37° C., however, this temperature varies by about±1° C. from individual to individual due to differences in metabolic rate, age, and hormonal influences. The normal human core temperature undergoes a regular circadian fluctuation of 0.5–0.7° C. In individuals who sleep at night and are awake during the day, the temperature is lowest during sleep, slightly higher in the awake but relaxed state, and rises with activity. In women, there is an additional monthly cycle of temperature variation characterized by a rise in basal temperature at the time of ovulation. Temperature regulation is less precise in young children, and they may normally have a core temperature that is 0.5° C. or so above the established norm for adults.

Various parts of the body are at different temperatures, and the magnitude of the temperature difference between the parts varies with the environmental temperature. The rectal temperature is representative of the temperature at the core of the body and varies least with changes in environmental temperature. The extremities are generally cooler than the rest of the body and, within a particular body part, the tissue temperature is lowest at the skin surface.

Variations in tissue temperature affect other physiological variables, such as the perfusion rate. A rise in tissue temperature triggers a homeostatic reflex, which enhances local blood flow in order to increase transfer of heat away from the skin. Cooling the tissue to approximately 25° C. decreases the perfusion rate; however, at much lower temperatures the skin again takes on a ruddy color. Other factors, such as activity, infections, some malignancies or mental stress, can also modulate the perfusion rate. A familiar example is the change in skin coloration, which can accompany exercise, alcohol intake, or even a change in position from sitting to standing.

In order to fully appreciate the effects of temperature variations on NI measurements, it is helpful to review the theoretical description of light propagation in tissues. A discussion of optical properties of tissue and the effect of these properties on light scattering and absorption is provided below. The dependence of NI measurements on temperature of the tissue is also illustrated, and preferred embodiments for controlling the temperature of NI measurements are described.

For clear or highly absorbing samples, Beer's law describes the light fluence within a sample as follows:

$$I=I_o exp-(\mu_t z) \tag{1}$$

where I represents the light fluence at a distance, z, into the sample, $I_o$ represents the incident intensity and $\mu_t$ represents a total attenuation coefficient. $\mu_t$ is the sum of the absorption coefficient, $\mu_a$, and the scattering coefficient, $\mu_s$. The mean free path of a photon describes the average distance traveled by a photon between absorptive or scattering events and is defined as $1/\mu_t$.

At visible and NIR wavelengths, scattering dominates absorption in biological tissues (i.e., $\mu_s >> \mu_a$), and photon propagation deviates significantly from Beer's law. Tissue scattering occurs because of a mismatch between the index of refraction of the extracellular fluid (ECF) or intracellular fluid (ICF) and the cellular membranes of the tissue. As used herein, the expression "cellular membranes" encompasses both the cell membrane as well as the membranes of organelles, such as mitochondria or collagen fibrils. Besides undergoing scattering and absorption, photons can be reflected at the tissue/air interface; photons can also be re-emitted out of the tissue.

An exact assessment of light propagation in tissues would require a model that characterizes the spatial and size distributions of tissue structures, their absorbing properties, and their refractive indices. For real tissues, such as skin, the task of creating a precise representation of photon migration from the solution of Maxwell's electromagnetic (EM) wave equations is formidable. Consequently, it is necessary to rely upon mathematical approximations in order to simplify the calculation of optical properties of tissue.

One useful approach for describing the transfer of light energy through a turbid medium uses radiative transport (RT) theory. In the RT formalism, light propagation is considered equivalent to the flow of discrete photons, which may be locally absorbed by the medium or scattered by the medium. For dense media where the detector distance is large relative to the photon mean free path, RT theory can be simplified to yield the Diffusion Theory (DT) approximation. DT describes photon propagation in tissues by the absorption coefficient, $\mu_a$, and the reduced scattering coefficient $\mu_s'=\mu_s[1-g]$, where the anisotropy factor, g, represents the average cosine of the angle at which a photon is scattered. Typical values of g for tissues are $0.9<g<1.0$ (forward scattering). The attenuation of photons in tissues is described by an effective attenuation coefficient, $\mu_{eff}$, as follows:

$$\mu_{eff}=\sqrt{(3 \mu_a(\mu_a+\mu_s'))}=\sqrt{(3 \mu_a[\mu_a+\mu_s(1-g)])} \tag{2}$$

The value of $\mu_{eff}$ can be calculated from scattering measurements (such as SRLS) and both $\mu_a$ and $\mu_s'$ can be derived from measurements of $\mu_{eff}$ under different conditions. In turn, changes in the values of $\mu_a$ and $\mu_s'$ can be related to tissue parameters, such as the concentration of an analyte.

For tissue samples irradiated at visible and NIR wavelengths, the size of the scattering material is near the wavelength of light, and the reduced scattering coefficient, $\mu_s'$, can be expressed using Mie theory as follows:

$$\mu_s'=\mu_s(1-g)=3.28\pi a^2 \rho(2\pi a n_{ex}/\lambda)^{0.37} (m-1)^{2.09} \tag{3}$$

where ρ represents the volume density, number of particles per unit volume, a represents the radius of the scattering particle (e. g., cells, mitochondria, or collagen fibrils), $n_{ex}$ represents the refractive index of the medium (ECF or ICF), and m=$(n_{in}/n_{ex})$ which is the ratio of the refractive index of the scattering particle $n_{in}$ to $n_{ex}$. See Graaf, et al., "Reduced light-scattering properties for mixtures of spherical particles: a simple approximation derived from Mie calculations", APPLIED OPTICS, Vol. 31, No. 10, Apr. 1, 1992. Light fluence within the sample is described by the following formula:

$$I=I_o exp-(\mu_{eff} z) \tag{4}$$

where I, $I_o$, and z are defined as above and $\mu_{eff}$ is defined as above and differs from the total $\mu_t$ defined in Equation (1).

For a given incident wavelength, $\mu_s'$ changes with either the cell size, a, or the refractive index ratio m, as shown in equation 3. Because the refractive index of the cellular membranes, $n_{in}$, remains relatively constant, $\mu_s'$ is influenced mostly by $n_{ex}$ and a. For example, glucose reduces tissue scattering by decreasing the refractive index difference between the ICF/ECF and the cellular membranes. Variations in $n_{ex}$ are not specific for a particular analyte, however, and are affected by any change in the total concentration of solutes in the ECF, including hemoglobin. $n_{ex}$ is also susceptible to changes in physiological variables, such as temperature of the tissue.

Methods of determining $\mu_{eff}$, $\mu_s'$, and $\mu_a$ are known in the art. One of these methods is the measurement of diffuse reflectance of the skin tissue. In a diffuse reflectance measurement, the measured reflectance has the following functional dependence:

$$R_d=f(\mu_s', \mu_a, n_s/n_0)$$

where $\mu_s'$ represents the reduced scattering coefficient, $\mu_a$ represents the absorption coefficient, $n_s$ represents the refractive index of the scattering medium and $n_0$ represents the refractive index of the surrounding layer, usually air.

Another method of measuring the absorption and scattering coefficients is known as spatially resolved diffuse reflectance, R(r). In this method, the intensity of the reflected light is measured at several distances from the point at which light is injected. The intensity of the reflected light at a given distance R(r) is related to the separation of the source and detector by the relationship:

$$R(r)=K_0[exp(-\mu_{eff} r)]/r$$

A plot of Log r times R(r) vs. r yields a line with a slope of $\mu_{eff}$. Other methods for determination of determination optical properties of tissues are described in the art. These methods include collimated transmittance and frequency domain measurements.

The present invention involves methods and devices for eliminating the effects of physiological and spectral variables on measurements of $\mu_a$ and $\mu_s'$. Specific descriptions of the mechanisms by which temperature affects these parameters are provided below.

Temperature fluctuations affect the sensitivity and selectivity of NI measurements by influencing physiological and spectral variables. For example, temperature affects perfusion rates, which alter the concentrations of blood-borne spectral variables, such as hemoglobin, water, and electrolytes. These spectral variables can introduce measurement inaccuracies. However, it has been found that the magnitude of these inaccuracies can be reduced by compensating factors. IR backscattering measurements may be used to measure hemoglobin, total protein, HDL, and triglycerides in tissues. Temperature-controlled IR measurements thus yield a more accurate measure of glucose concentration by increasing the measurement accuracy of important spectral variables.

Temperature also affects the refractive index of the ECF. Because approximately 90% of human tissue is water, the refractive index of ECF may be approximated by the refractive index of water which varies with temperature as:

$$n=1.3341+2.5185 \cdot 10^{-5} T - 3.6127 \cdot 10^{-6} T^2 + 2.3707 \cdot 10^{-8} T^3$$

where n represents the refractive index and T represents the temperature. Changes in osmolarity of the ECF can also change the size of the cells due to osmotic swelling and shrinkage.

Because water is the main constituent of biomedical samples, its optical properties (in particular its absorption coefficient) are important parameters for NI measurements. Temperature variations contribute to the background noise in NI measurements by altering the intensities as well as the frequencies of the dominant water absorption bands. Changes in the absorption and scattering properties of the sample produce a variable optical path length, which affects all NI measurements.

Depolarization is a process in which completely polarized light is coupled to unpolarized light and is defined as $$D = \frac{\text{Polarized Light}}{\text{Total Incident Light}}$$

In turbid media, an incident polarized light beam undergoes multiple scattering events. The polarization of the incident beam is degraded with each scattering event, and the depolarization is affected by the number of scattering events in the medium. Because temperature influences the overall refractive index, the number of scattering interactions changes with varying tissue temperature. As the number of scattering interactions increases, the polarized light becomes progressively depolarized.

The following non-limiting examples further illustrate the present invention.

EXAMPLES

Example 1

Figure 2:
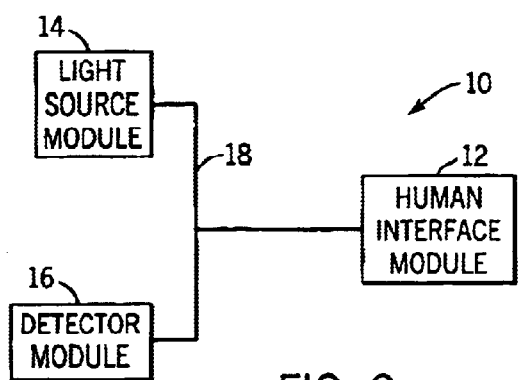
FIG. 2 is a schematic diagram of the temperature-controlled backscattering system of the present invention.

FIG. 2 is a schematic diagram of one embodiment of the temperature-controlled backscatter system 10 (TCBS) of the present invention. The TCBS comprises three modules: a human interface module 12; a light source module 14; and a detector module 16. As shown in FIG. 2, the human interface module 12 is connected to the light source module 14 and the detector module 16 via a bifurcated optical fiber probe 18.

Figure 3A:
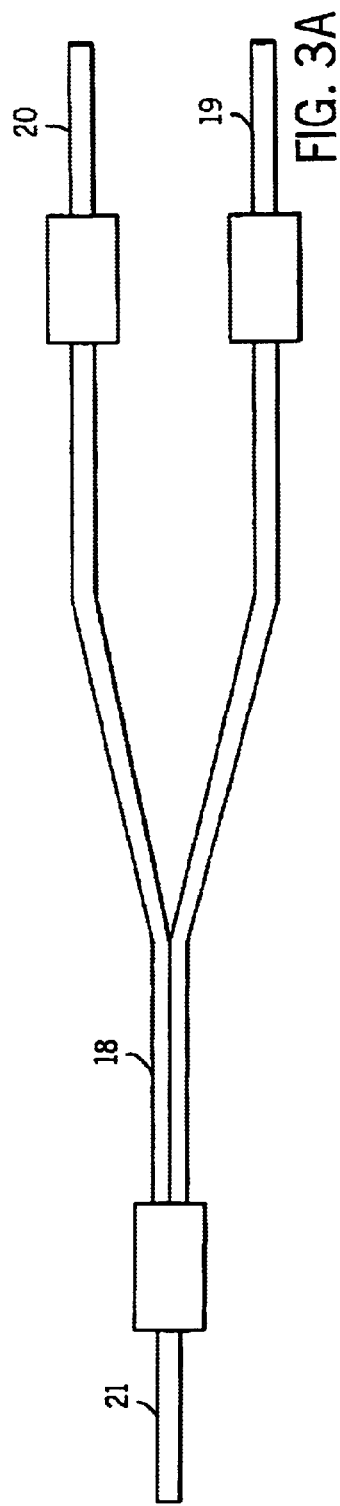
FIG. 3A is a diagram illustrating the bifurcated optical fiber probe of FIG. 2.
Figure 3B:
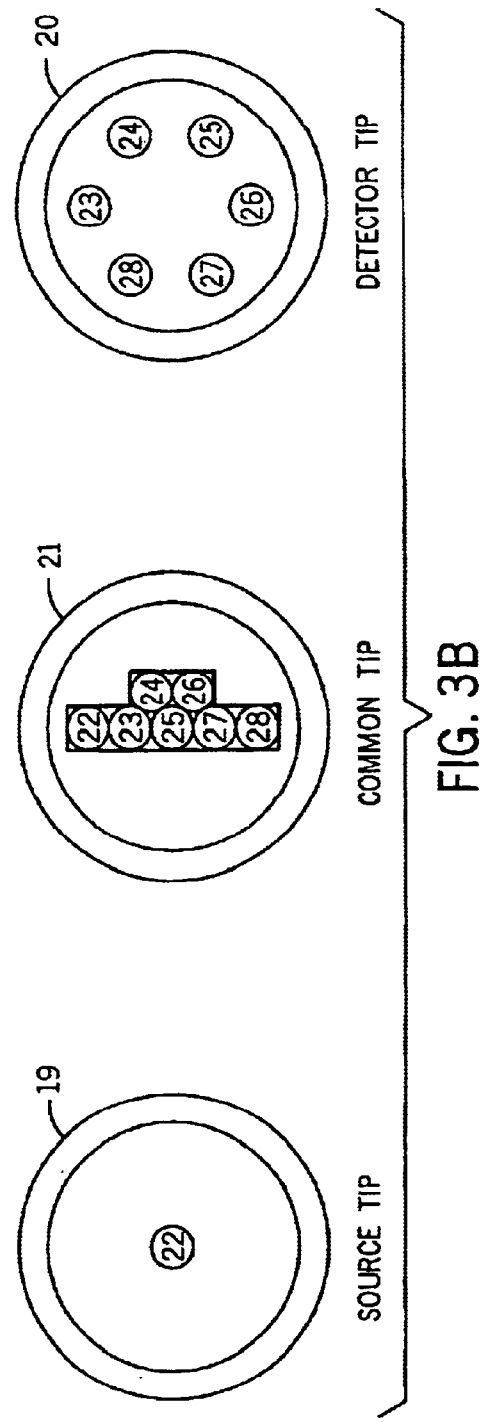
FIG. 3B is a series of diagrams showing portions of the bifurcated optical probe of FIG. 3A.

FIG. 3A is a detailed illustration of the bifurcated optical fiber probe 18. The bifurcated optical fiber probe is constructed from Anhydrous G Low OH VIS-NIR optical fibers. The bifurcated optical probe 18 comprises a source tip 19, a detector tip 20, and a common tip 21. The three distinct termination points or "tips" of the bifurcated optical probe are shown in FIG. 3B. During operation, the source tip 19 is contained within the light source module 14, the detector tip 20 is contained within the detector module 16, and the common tip 21 is contained within the human interface module 12. A single optical fiber 22 transmits light from the source tip 19 to the common tip 21. Six optical fibers 23, 24, 25, 26, 27, and 28 transmit light from the common tip 21 to the detector tip 20.

Light source module 14 includes a source of modulated light (not shown), such as a Gilway L1041 lamp modulated with a Stanford Research Optical Chopper. A prism, a dichroic beam splitter, or the like may be used to direct a portion of the beam emanating from the light source to a reference detector, such as a Hammamatsu S-2386-44K 6C Silicon Detector, in order to normalize the measurements for fluctuations in source intensity. The rest of the light emanating from the light source is focused onto the end of the source tip by means of at least one focusing lens. Additional optical elements, such as attenuators, optical filters, and irises may be inserted between the light source and the source tip. The source tip is preferably held in an adapter having provisions for adjusting the location of the source tip with respect to the beam emanating from the light source.

The common tip 21 is installed in the human interface module, which is placed against a body part during use. As shown in FIG. 3B, the common tip comprises the source fiber 22 and six additional fibers 23, 24, 25, 26, 27, and 28 that collect the light that is scattered by the tissue sample.

Figure 4:
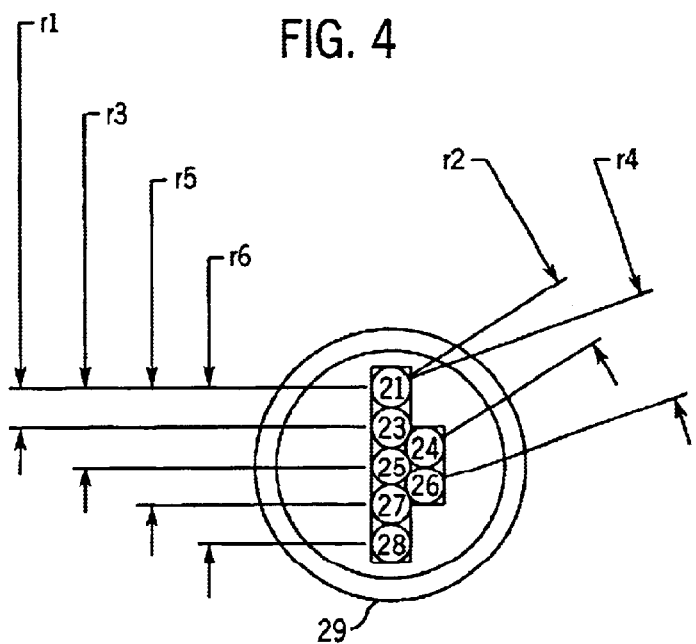
FIG. 4 is a diagram illustrating the nominal separation distances, r, between collection fibers 2–7 and the excitation fiber 1.

The collection fibers 23, 24, 25, 26, 27, and 28 are located within the common tip 21 at increasing distances from the source fiber 22. The nominal separation distances, r, between the center of the source fiber 22 and the centers of the collection fibers 23, 24, 25, 26, 27, and 28 of the common tip 21 are shown in FIG. 4. An important aspect of the present invention is that all of the collection fibers are located at separation distances, r, that are less than mm away, and, preferably, less than 2 mm away from the source fiber 22. As will be more thoroughly described below, locating the fibers in this manner results in enhanced precision and accuracy over the methods used in the prior art.

The collection fibers 23, 24, 25, 26, 27, and 28 are arranged in a circle within the detector tip 20, as shown in FIG. 3B, with sufficient spacing to allow a shutter to interrogate each fiber individually. The detector module receives the detector tip 20 and holds it adjacent to a rotating shutter (not shown) that allows detection of the light emitted from one fiber at a time. The shutter has a detent or other means to lock it in the six fiber positions. The light from the fiber of interest is focused on a detector by a pair of 25 mm diameter, 60 mm focal length Achromatic lenses. The detector was a Hammamatsu S-2386-44K 6C Silicon Detector or any other equivalent detector. The detector module also comprises appropriate electronic signal processing instrumentation such as large dynamic range amplifiers and lock-in amplifiers. Alternatively, the outputs of the six fibers can be directed to six detectors for parallel signal processing.

Figure 5:
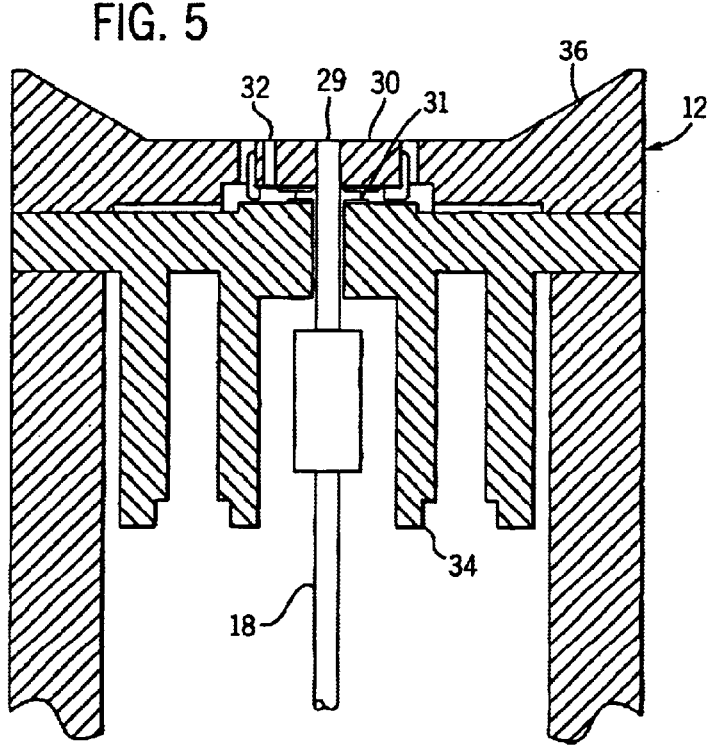
FIG. 5 is a schematic diagram of the human interface module of the temperature-controllable backscattering system of the present invention.

FIG. 5 illustrates the human interface module 12, which comprises an aluminum disk 30, a thermoelectric cooling element 31, a thermocouple 32, a heat sink 34, the common tip 21, and an interface adapter 36. The aluminum disk contains a through-hole that receives the common tip 21 of the fiber optic probe and holds the common tip 21 against the body part. The temperature of the aluminum disk 30 (and of the tissue adjacent the disk 30) is controlled by a thermoelectric cooling element 31, such as a Marlow Industries model number SP1507-01AC. The thermoelectric cooling element 31 is powered by a temperature controller/power supply, such as a Marlow Industries model number SE5000-02. A heat sink 34 is provided on the back of the thermoelectric cooling element 31 to enhance heat transfer. The interface adapter 36 is shaped to conform to a body part and may, for example, be cylindrical, flat, spheroidal or any other shape that provides efficient optical and thermal coupling to a body part.

Example 2

Figure 6:
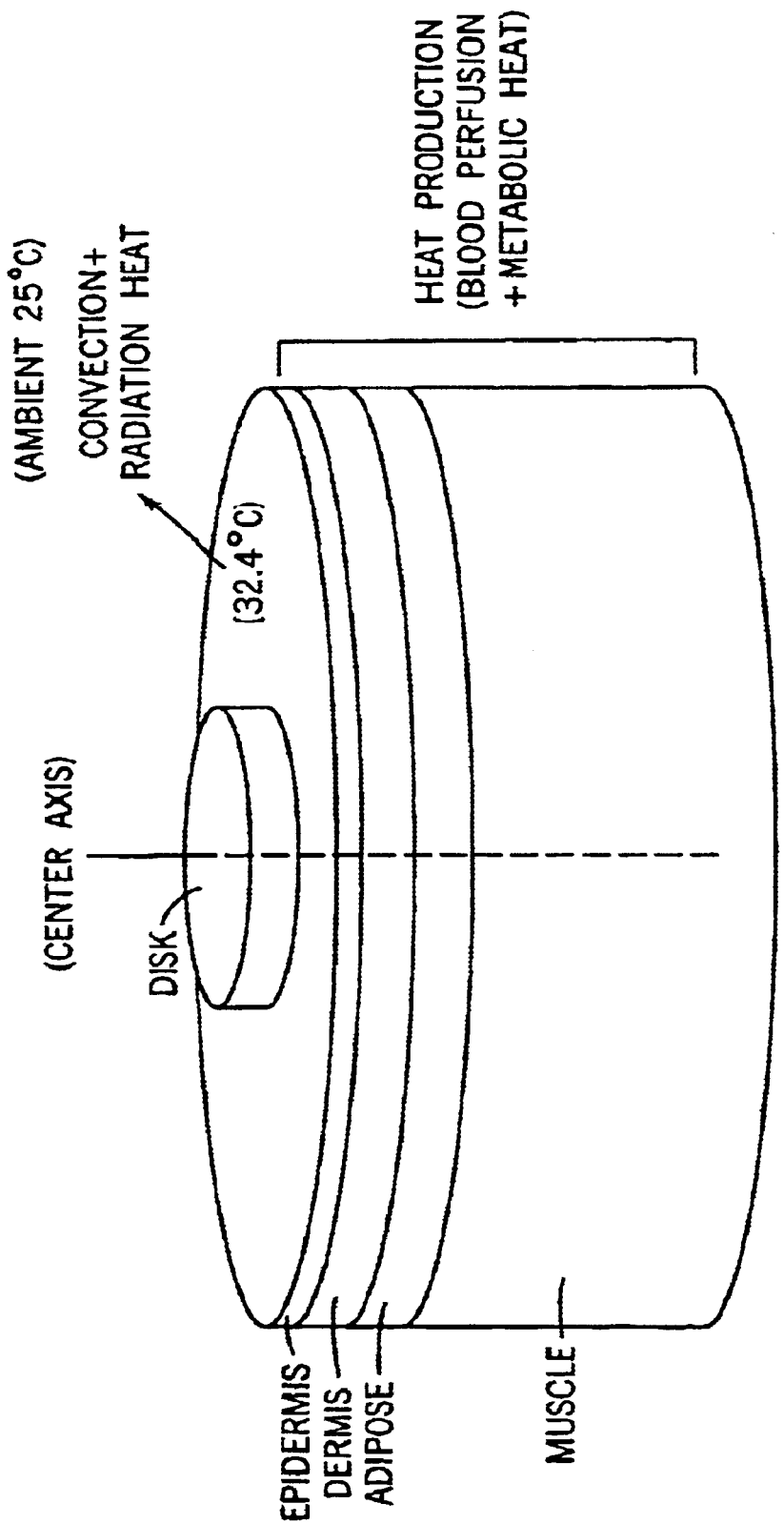
FIG. 6 is a schematic diagram of a thermal model of a human forearm.

FIG. 6 illustrates assumptions made for a mathematical model of the human interface module and the underlying tissue sample. The tissue sample is modeled as a multi-layer sample wherein each of the layers has different thermal transfer properties. In the absence of the interface module, the tissue temperature changes along a gradient from an interior body physiological temperature of approximately 37° C. (muscle) to a typical skin surface temperature of 32.4° C. (epidermis).

Figure 7A:
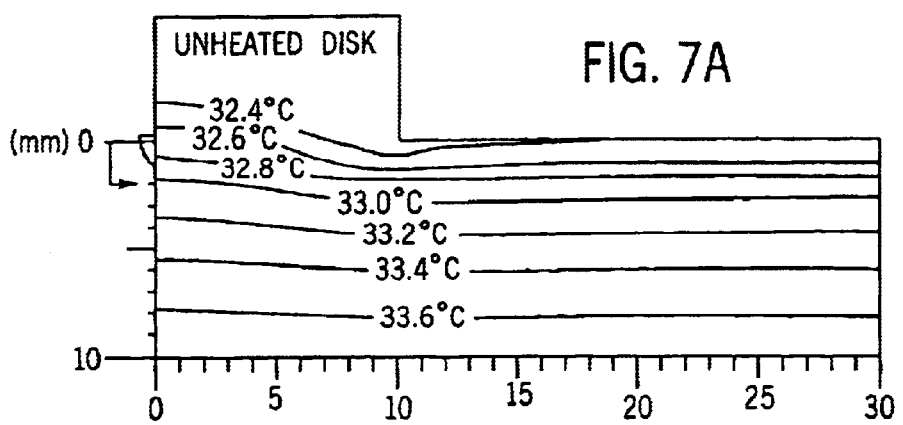
FIGS. 7a, 7b, and 7c are schematic diagrams illustrating the temperature gradients as a function of penetration depth and lateral distance results of the thermal model of a human forearm.
Figure 7B:
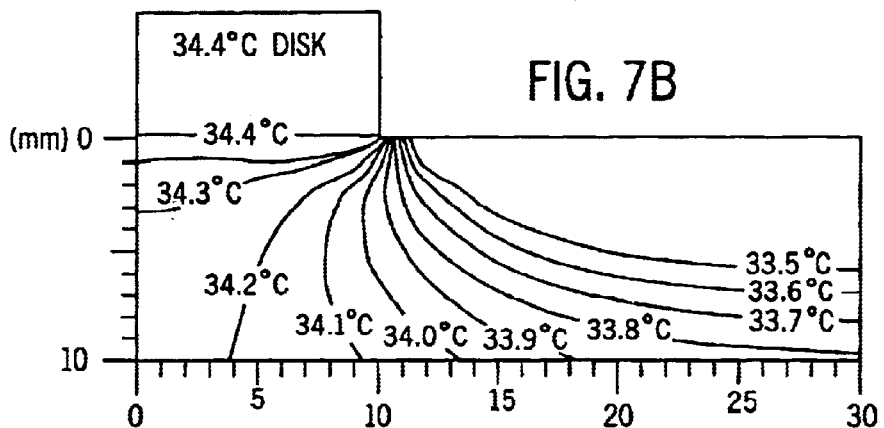
Figure 7C:
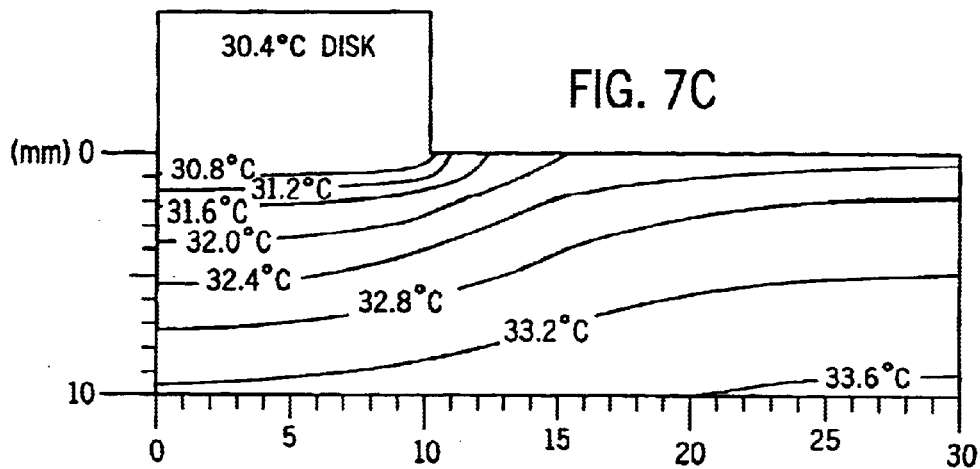

FIGS. 7a through 7c show model values of steady-state temperatures within an axisymmetric cross-section of the model. Each figure represents a different temperature condition imposed by the interface module (i. e., the disk). The figures also place a dimensional scale along the edges of the model to indicate values of tissue depth (up to 10 mm from the tissue surface) and radial distance (up to 30 mm from the central axis of the disk).

FIG. 7a presents the situation when a disk made of an insulating material such as Plexiglas is brought in contact to the tissue surface. The disk is not capable of controlling temperature. The disk insulates the underlying tissue from its ambient surroundings and causes a minor increase in epidermal temperature from 32.4° C. to about 32.7° C. At a depth of 2 mm below the tissue surface, the temperature is about 33.0° C. on the center axis. The resulting tissue temperature gradient 0.6° C. is somewhat smaller than the natural state wherein no insulating disk is applied. As shown by Quan and Wilson, a 0.5° C. temperature difference affects the scattering signal by an amount equivalent to 90 mg/dL change in glucose concentration. This represents a model for an insulating detection probe having no temperature control. The insulating probe head model offers a minor advantage for the non-invasive measurement of an analyte.

Figure 8:
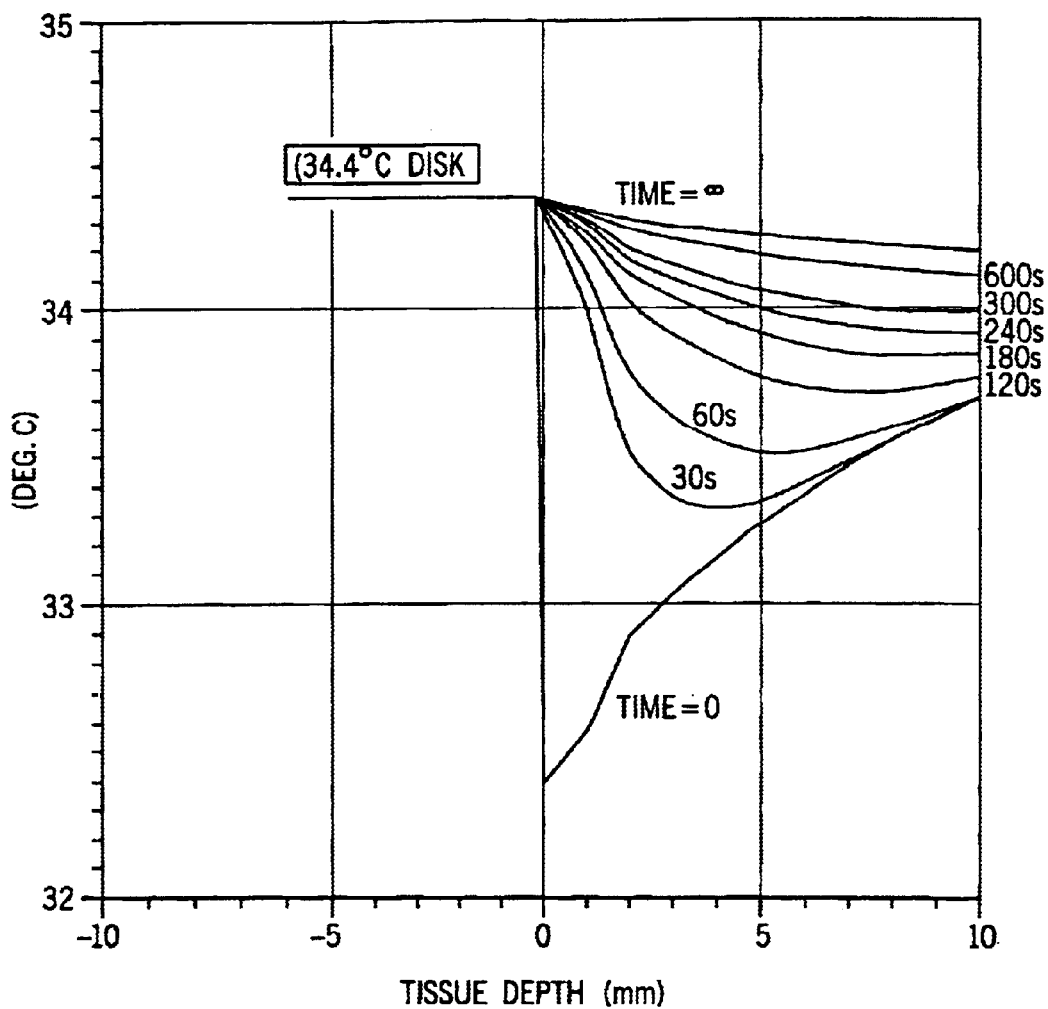
FIG. 8 is a graph illustrating the temperature gradients over time predicted by a thermal model of the tissues adjacent to temperature-controllable backscattering system of the present invention.

In FIG. 7b a heat conducting disk 30 maintained at a constant temperature of 34.4° C. is applied to the surface of the tissue. The disk maintains the temperature of the epidermis at 34.4° C., which temperature is lower than the body physiological temperature. At a depth of 2 mm below the surface of the tissue, the temperature is 34.3° C. The disk produces a tissue temperature gradient of 0.1° C., which is substantially smaller than the natural state. At a depth of 2 mm, temperature is maintained within a 0.1° C. at lateral distances up to 5 mm from the axis. At a depth of 1 mm, temperature is maintained within 0.1° C. at lateral distances up to 8 mm from the axis. The time required for the tissue to reach this condition (after the skin is brought in contact with the disk) is shown in FIG. 8. In FIG. 8, the model temperatures along the central axis just prior to the moment the skin touches the heat conducting disk is shown and is labeled as Time=0. In the time period ranging from 30 seconds to 600 seconds after contact between skin and the heat conducting disk, the tissue (dermis) temperature rises and the temperature gradient decreases until an essentially constant value is achieved. The calculated temperature gradient reaches 0.2° C. at a depth of 2 mm, after a 60 second equilibration period. At 600 seconds, the temperature gradient flattens out and approaches the steady-state value labeled as Time=infinity.

In FIG. 7c a heat conducting disk having a constant temperature of 30.4° C. is brought in contact with the tissue surface. Interaction with the disk reduces the epidermal temperature to 30.4° C. Temperature is calculated to be 30.8° C. at a depth of approximately 1 mm and 31.5° C. at a depth of 2 mm below the surface of the tissue. The temperature gradient is 0.4 C. at a depth of 1 mm and 1.1° C. at a depth of 2 mm. This gradient is greater than the gradients shown in FIGS. 7a and 7b. However, temperature was calculated to be constant in the horizontal plane up to distance of 5 mm.

The probe design described herein is particularly well adapted for temperature-controlled SRLS measurements. When the probe temperature is held at 34.4° C. (i. e., 2° C. above the natural temperature of the surface of the skin), the underlying tissue temperature does not vary by more than 0.2° C. up to a depth of 2 mm below the surface of the tissue (except at the extreme edges of the disk, where no SRLS measurements are taken). Furthermore, the tissue temperature does not vary by more than 0.1° C. within a depth of 2 mm and a radial distance of less than 4 mm from the central axis of the disk. Closer control of temperature and less of a temperature gradient is maintained at 0.1 mm below the surface of the skin. Greater penetration depths would encounter a volume of tissue having a greater range of temperatures, thereby decreasing the reproducibility of the SRLS measurement.

Photon path in a turbid medium can be expressed by the radiation transport equation. This analytical equation is difficult to solve. An approximation for solving the equation is the diffusion theory approximation. The diffusion theory approximation is limited to cases where the light has been highly scattered (i. e., the approximation is limited to situations in which a photon is scattered many times before it is absorbed or detected). The condition of multiple scattering depends upon the average distance between scattering centers (density of scattering material) and on the ratio of scattering to total attenuation known as optical albedo $(\mu_s/\mu_s+\mu_a)$. The source-tissue-detector geometry and the boundary conditions of the medium are important for the application of the diffusion theory approximation. For SRLS measurements, the conditions require that the separation between the source and the detector be much greater than the transport optical mean free path, the mean distance between two successive absorption or scattering interactions in the medium $[1/(\mu_a+\mu_s')]$. For tissues with small absorption coefficients (1 cm$^{-1}$) and a scattering coefficient of 10 cm$^{-1}$, the mean free path in the near IR is 1 mm. Diffusion theory approximation applies at source-to-detector distances much larger than 1 mm, typically 1 cm and up to 7 cm. Measurement at a great distance from the source is referred to as the far field condition. Mean free paths between interaction sites between photons and tissue typically range from 0.01 mm to 2 mm, with 0.75 mm being a typical value in the visible spectrum. In the present invention, the detector distances can be as short as 0.4 mm to 5 mm. Thus, they are either shorter than or of a comparable value to the mean free path, and the diffusion theory approximation does not hold. Measurements at small separations of source and detector present a near field condition.

A more exact solution of the light transport equation in turbid media can be obtained by following the path of each individual photon and calculating the probability of scattering and/or absorption in a series of steps using Monte Carlo simulation. Physical quantities of interest are scored within statistical uncertainties of the finite number of photons simulated. The power of the Monte Carlo method lies in its ability to handle virtually any source, detector, and tissue boundary condition, as well as any combination of optical properties of tissue. Monte Carlo methods can also accommodate polarized light and diffraction effects in the light propagation calculation, and these methods are preferred in the present invention over the diffusion theory approximation.

Monte Carlo simulations were used for the probe geometry of the present invention. The public domain software program employed was "Monte Carlo simulations of multi-layered turbid media", by Lihong Wang and Steven L. Jacques, obtained from Oregon Laser Center, Portland, Oreg.

Figure 9:
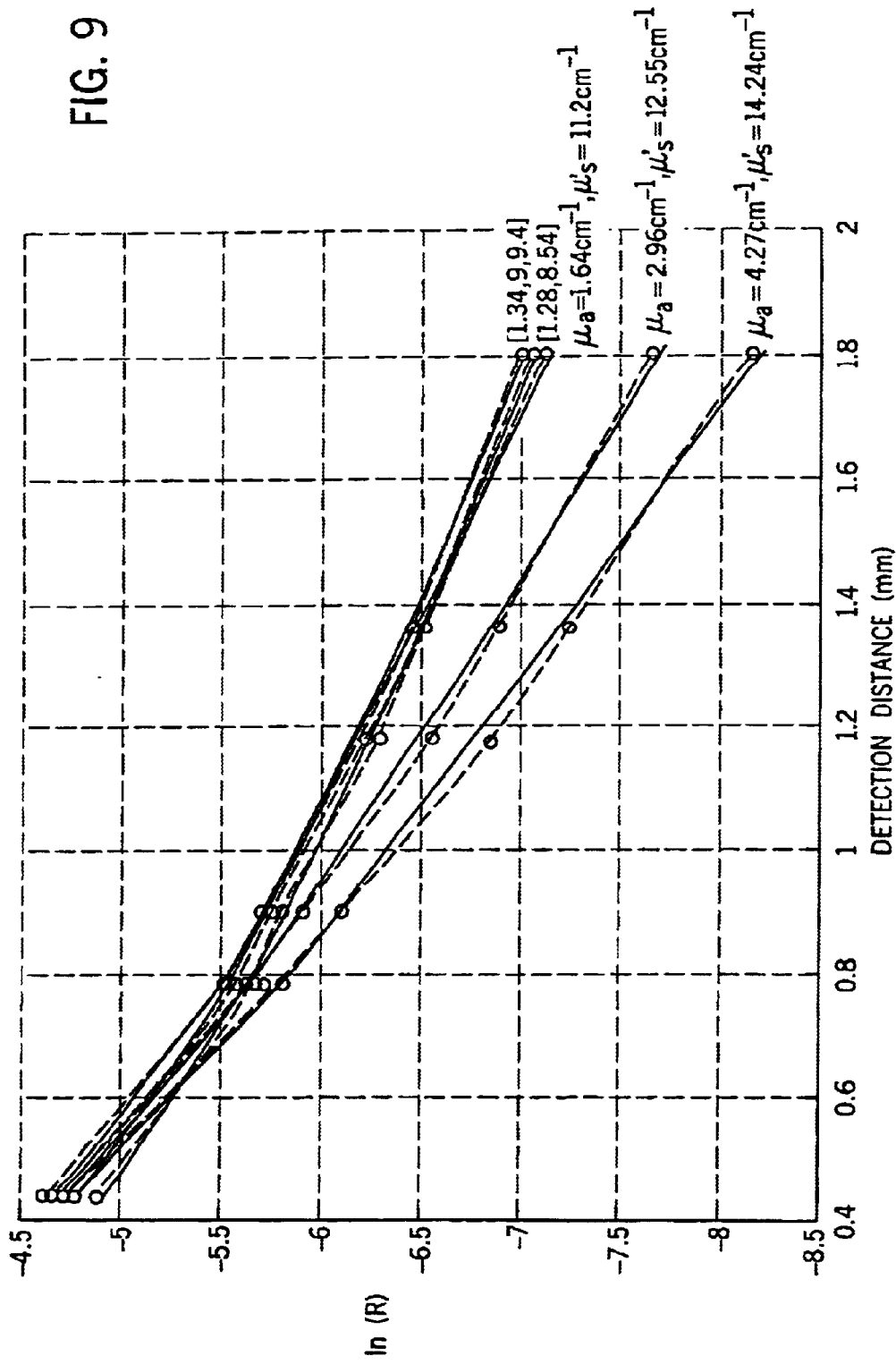
FIG. 9 is a graph illustrating a Monte Carlo simulation and the measured reflectance for human volunteers.

In the Monte Carlo model, the beam diameter was 400 micrometers, the number of photons injected was 200,000 per run, light was propagating from fiber (n=1.5) into tissue (n=1.4). The thickness of the tissue layer was set from 5 to 25 mm. Light reflected at the 0.44 mm, 0.78 mm, 0.89 mm, 1.17 mm, 1.35 mm, and 1.81 mm distances from the point the light was injected were calculated for a matrix of several $\mu_s'$ and $\mu_a$ values. These distances corresponded approximately to the positions of fibers 23, 24, 25, 26, 27, and 28. The resultant $\log_e R(i)$ vs $\log_e (R_i/R_j)$ were plotted as a grid. The constant $\mu_a$ and $\mu_s$ points were connected to form a grid in the $\log_e R(i)$ vs $\log_e (R_i/R_j)$ space, where R(i) represents reflectance at a distance I and R(j) represents reflectance at a distance j. Spatially resolved backscattering was determined for a set of Intralipid solutions, hemoglobin solution in Intralipid suspension, opal glass, and plastic rods polymerized to incorporate different levels of scatter and absorbing pigment. The experimental values were overlapped on the Monte Carlo-generated grid, and absorption and scattering coefficients of the reference material were determined by the use of tables generated from the grid. Spatially resolved light scattering (SRLC) measurements were obtained on the dorsal part of the forearms of human volunteers and plotted on the same graph. An example of the result of Monte Carlo simulation and the measured reflectance for a human volunteer are shown in FIG. 9. The dashed lines connecting the circles represent experimental data. The solid lines represent Monte Carlo fits for the absorption and scattering coefficients indicated. The graph indicates that the reflectance values predicted by the model are close to the experimental results. $\mu s'$ and $\mu_a$ values for several Caucasian, Oriental and Mediterranean subjects were determined at 34° C. The average values of $\mu_s'$ and $\mu_a$ at several illumination wavelengths were used to calculate the mean free path (mfp') and are shown in Table 1.

TABLE 1

| Optical constant | Average optical constants and mean free path for human subjects | | | | | |
|---|---|---|---|---|---|---|
| | 550 nm | 590 nm | 650 nm | 750 nm | 800 nm | 900 nm |
| $(\mu_s' + \mu_a)$ (mm$^{-1}$) | 16 | 14 | 11 | 10 | 9 | 8 |
| mean free path (mm) | 0.62 | 0.72 | 0.88 | 1.03 | 1.1 | 1.23 |
| Penetration depth (mm) | 0.72 | 0.92 | 1.42 | 1.67 | 1.92 | 2.04 |

Thus the measured mean free path is of the same magnitude as the separation of the source from the detector, thereby justifying the use of Monte Carlo modeling. The penetration depths achieved were less than or equal to 2 mm. The majority of the reflected light sampled at depths in the skin less than or equal to about 2 mm. Other longer wavelengths up to 2500 nm can be selected to achieve shallow penetration depth.

The effect of changes of temperature on the scattering and absorption coefficients of a diabetic and a non-diabetic individual were tested by means of the SRLS apparatus described in Example 1, and absorption and scattering coefficients were determined from the Monte Carlo-generated grid. Temperature of the tissue was varied from 20° C. to 45° C. Concentrations of glucose and hemoglobin in blood were measured by means of a commercial instrument (Vision®, Abbott Laboratories) prior to the SRLS measurement. Glucose concentration in the nondiabetic subject was 88 mg/dL and glucose concentration in the diabetic subject was 274.6 mg/dL. SRLS measurements were performed on the forearm of each subject.

The reduced scattering coefficient increased with increased temperature at all wavelengths for the two subjects. $d\mu_s'/dT$ ranged from 0.044 to 0.0946 for the non-diabetic subject and from 0.0633 to 0.0881 cm$^{-1}$/° C. for the diabetic subject. The change in the refractive index of water over the same temperature range was approximately $-1 \times 10^{-4}$ per ° C. The change in the reduced scattering coefficient for 1000 nm spherical particles over the same temperature range is calculated using the equation of Graaf et al (Equation (3)) to be 0.024 cm$^{-1}$ per ° C. Thus the measured $d\mu_s'/dT$ for the forearm of the test subjects is larger than the calculated values for 1000 nm particles, which mimic the biological tissue. Dependence of the scattering coefficient (in tissue) on temperature is greater than dependence of the scattering coefficient (in 1 mm particles) on temperature, which, in turn, is much greater than dependence of refractive index on temperature.

Figure 10:
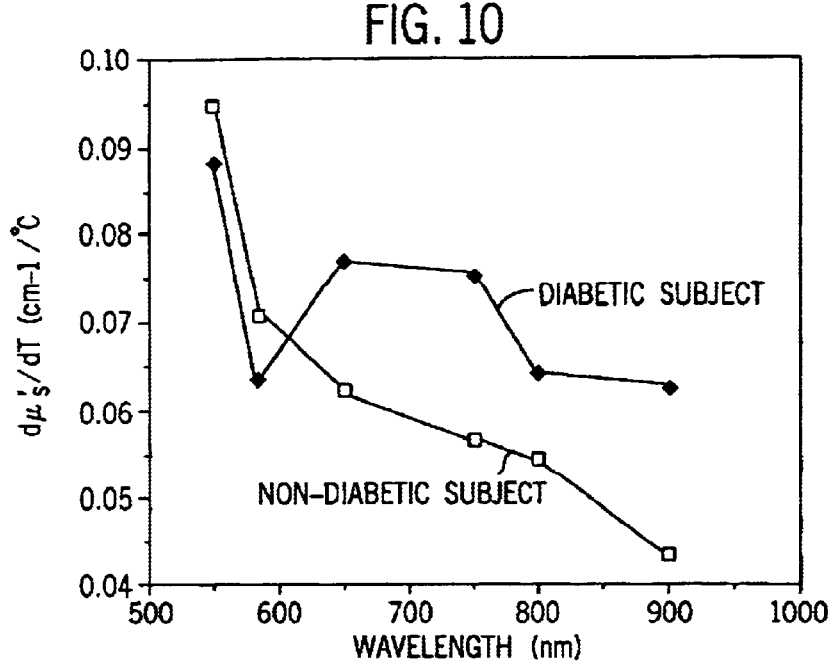
FIG. 10 is a graph illustrating spectral distribution of spatially resolved scattering data from a diabetic subject and a non-diabetic subject.
Figure 11:
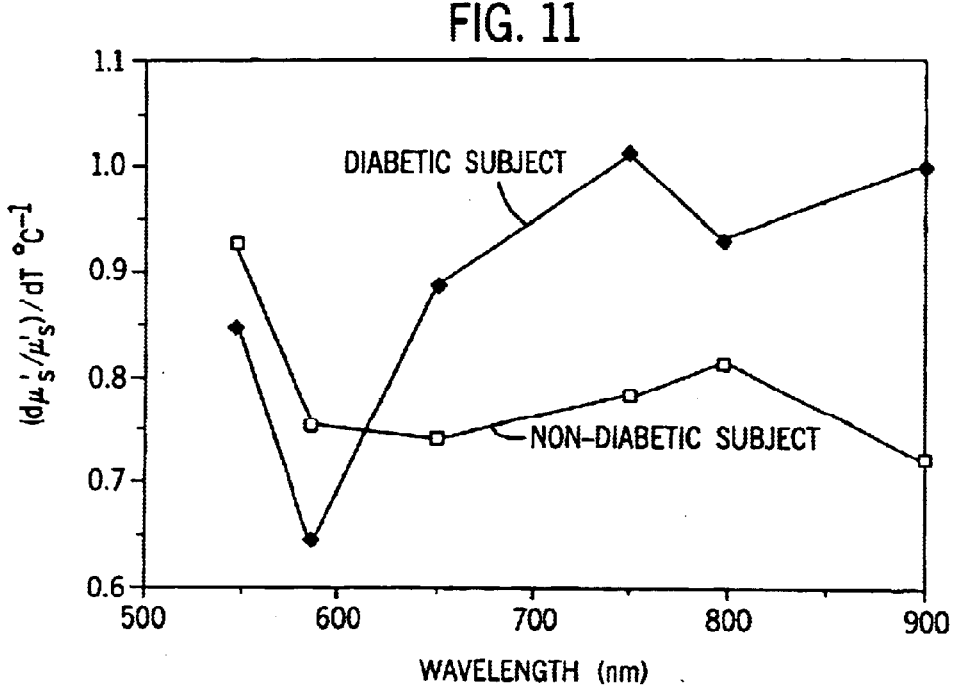
FIG. 11 is a graph illustrating spatially resolved scattering data, spectral distribution of the partial change in the scattering coefficient with respect to temperature, from a diabetic subject and a non-diabetic subject.

FIG. 10 shows the spectral distribution of the derivative of scattering coefficient with respect to temperature ($d\mu_s'/dT$) for the two subjects. A difference in the spectral response between the two subjects can be observed. The fractional change in the derivative is shown in FIG. 11. A noticeable difference between the two subjects was observed, especially at the non-absorbing wavelengths (away from the visible hemoglobin absorption bands).

Figure 12:
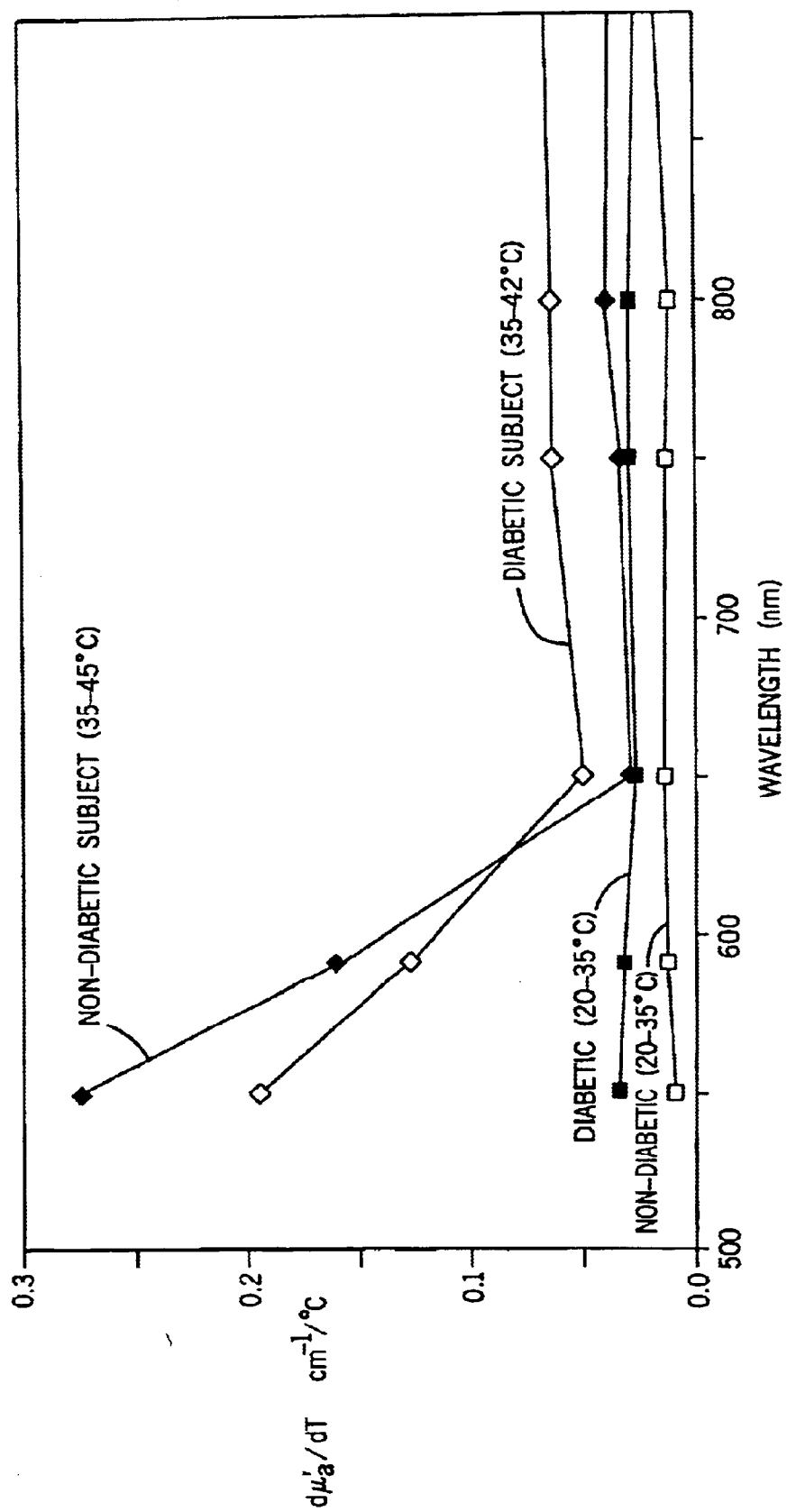
FIG. 12 is a graph illustrating spatially resolved scattering data, spectral distribution of the change in absorption coefficient with respect to temperature, from a diabetic subject and a non-diabetic subject.

The derivative of the absorption coefficient with respect to temperature is shown in FIG. 12 for the two subjects. The spectral distribution of the derivative $d\mu_a/dT$ differs between the two temperature ranges of 20 to 35° C., and 35 to 40° C. At temperatures below 35° C. (the ambient skin temperature), slight change in the $d\mu_a/dT$ as a function of temperature can be observed. However, the values differed for the two subjects. At temperatures above 35° C., the absorption derivative at the hemoglobin visible absorbing wavelengths is much higher than that at the non-absorbing wavelengths, which suggests a change in blood perfusion. The shape of the curve is similar to that of hemoglobin absorption. Blood perfusion to the skin at higher temperature may account for this similarity. There is an observed difference between diabetic and non-diabetic subjects.

Various modifications and alterations of this invention will become apparent to those skilled in the art without departing from the scope and spirit of this invention. It should be understood that this invention is not to be unduly limited to the illustrative embodiments set forth herein.

For example, while in-vivo glucose measurement has been illustrated, other measurements, in-vivo or in-vitro, needing improved specificity could benefit from measurements with combined technologies (i., e., alcohol, blood urea nitrogen (BUN), bilirubin, hemoglobin, creatine, electrolytes, blood gases, and cholesterol). It should be recognized that the wavelengths used for measurement may vary for the different analytes of interest.

A variety of detectors may be employed in the present invention without departing from the spirit of the invention. Preferably, the detectors should be optimized for the particular measurement to be made, with wavelength, cost, performance, and engineering design being considered. The detectors may be either single element or array detectors. While single element detectors are generally less costly and more amenable to frequency modulation and detection schemes, an alternative embodiment could use detector arrays, such as a photodiode array or a charge-coupled device (CCD) array, for multi-wavelength detection.

Various filters and the like that transmit only the wavelength(s) of interest may be placed in front of the detectors. Such filters may include, for example, dielectric filters, holographic filters, and tunable filters, such as an Acousto-Optic Tunable Filter (AOTF). Alternatively, frequency modulation may be used to distinguish the one measured signal from another. The development of detectors having sensitivities extending continuously from visible wavelengths into the infrared region will permit the use of a single detector, or detector array, over a large spectral range, without the need to switch detectors.

Although the optical detection method used in the examples is spatially-resolved diffuse reflectance, other methods that can lead to calculating the absorption and scattering coefficients of a turbid medium can be used by those skilled in the art. Thus any optical measurement that allows control of temperature over an area larger than the area of optical measurement can be used. An example of such a measurement is diffuse reflectance using randomized optical fiber bundles. Another example involves frequency modulation measurements using a high enough modulation frequency to allow measuring a phase angle change over a small separation of source and detector. Yet another modification would be the use of polarimetric measurements utilizing polarization-conserving fibers. Other methods of calculation can be used, such as neural networks and data mining methodologies.

For non-invasive measurements on a body part, the body interface module may be adapted to change the shape of the body part or to change the physical relationship between the transducers and the body part. For example, the body interface module might be adapted to increase the pressure applied to the body part by the transducer. Such a change might be made, for example, to alter local perfusion rates.

What is claimed is:

1. A method of determining at least one parameter of a region of tissue of a body having a temperature, said method comprising the steps of:
    (a) modulating said temperature of said region of tissue of said body part between at least two values of temperature, whereby temperature of said region of tissue of said body part is controlled;
    (b) introducing light at at least one wavelength into said region of tissue of said body part at a surface of said body part and measuring light that is reflected, scattered, absorbed, or emitted by said region of tissue of said body part from an average sampling depth that is confined within said temperature controlled region of tissue of said body part, said average sampling depth not exceeding about 2 mm;
    (c) measuring at least one optical property of said region of tissue of said body part, at at least on wavelength, as a function of temperature, to obtain an optical, measurement; and
    (d) analyzing the optical measurement of (c) to obtain a determination of said at least one parameter of said region of tissue of said body part, wherein said at least one parameter is the presence or concentration of glucose in said region of tissue of said body part.

2. The method of claim 1 wherein said at least one parameter is the presence of a tissue heterogeneity that has thermal properties different from those of adjacent tissue.

3. The method of claim 1, wherein said at least one parameter is a change in blood circulation.

4. The method of claim 1, wherein said at least one optical property is a scattering coefficient.

5. The method of claim 1, wherein said at least one optical property is an absorption coefficient.

6. The method of claim 1, wherein said optical measurement is performed at two or more wavelengths.

7. The method of claim 1, wherein the area of the body part subject to temperature control is at least two times the area of the body part being optically sampled.

8. The method of claim 1, wherein the area of the body part subject to temperature control is at least five times the area of the body part being optically sampled.

9. The method of claim 1, wherein said at least one wavelength is between 400 nm and 2500 nm, inclusive.

10. The method of claim 1, wherein said at least one wavelength is between 400 nm and 2500 nm, inclusive.

11. The method of claim 1, further comprising the step of correlating the measured optical property with the concentration of glucose in the region of tissue of said body part, said concentration determined by a method independent of steps (a), (b), (c), and (d).

12. The method of claim 11, wherein said step of correlating involves a method selected from the group consisting of least squares, partial least squares, and neural networks.

13. The method of claim 1, wherein said at least one optical property is reflectance.

14. The method of claim 1, wherein said at least one optical property is mean free path.

15. The method of claim 1, wherein said at least one optical property is effective attenuation coefficient.

16. The method of claim 1, wherein said at least one optical property is light penetration depth in tissue.

17. A method of measuring at least one parameter of a region of tissue of a body part at a give temperature, said method comprising the steps of:
    (a) decreasing the temperature of said region of tissue of said body part to a temperature that is at or below the normal physiological temperature of said region of tissue of said body part, whereby temperature of said region of tissue of said body part is controlled;
    (b) introducing light at at least one wavelength into said region of tissue of said body part at a surface of said body part and measuring light that is reflected, scattered, absorbed, or emitted by said body part from an average sampling depth that is confined within said temperature controlled region of tissue of said body part, said average sampling depth not exceeding about 2 mm;
    (c) determining at least one optical property of said region of tissue of said body part at said decreased temperature of step (a);
    (d) introducing light at at least one wavelength into said region of tissue of said body part at a surface of said body part and measuring light that is reflected, scattered, absorbed, or emitted by said body part from an average sampling depth that is confined within said temperature controlled region of tissue of said body part;
    (e) increasing the temperature of said region of tissue of said body part to a temperature above the normal physiological temperature of said region of tissue of said body part, whereby temperature of said region of tissue of said body part is controlled;
    (f) determining at least one optical property of said region of tissue of said body part at said increased temperature of step (e); and
    (g) analyzing the optical properties determined in steps (c) and (f) to obtain a measurement of said at least one parameter of said region of tissue of said body part, wherein said at least one parameter is the presence or concentration of glucose in said region of tissue of said body part.

18. The method of claim 17, wherein said at least one optical parameter is scattering coefficient.

19. The method of claim 17, wherein said at least one optical parameter is absorption coefficient.

20. The method of claim 17, further comprising the step of correlating the measured optical property with concentration of an analyte in the body, said concentration determined by a method independent of steps (a), (b), (c), (d), and (e).

21. The method of claim 20, wherein said step of correlating involves a method selected from the group consisting of least squares, partial least squares, and neural networks.

22. The method of claim 17 wherein said parameter is the presence of a tissue heterogeneity that has thermal properties different from those of adjacent tissue.

23. The method of claim 17, wherein said parameter is the presence of a blood circulation change.

24. The method of claim 17, further comprising the step of correlating the measured optical property with concentration of an analyte in the region of tissue in said body part, said concentration determined by a method independent of steps (a), (b), (c), (d), (e), (f), and (g).

25. The method of claim 24, wherein said step of correlating involves a method selected from the group consisting of least squares, partial least squares, and neural networks.

26. The method of claim 17, wherein said at least one optical parameter is reflectance.

27. The method of claim 17, wherein said at least one optical parameter is mean free path.

28. The method of claim 17, wherein said at least one optical parameter is effective attenuation coefficient.

29. The method of claim 17, wherein said at least one optical parameter is light penetration depth in tissue.

30. A method of measuring at least one parameter of a region of tissue of a body part, said method comprising the steps of:
  (a) adjusting the temperature of said region of tissue of said body part to a temperature that is substantially the same as the normal core temperature of said body part, whereby temperature of said region of tissue of said body part is controlled;
  (b) introducing light at at least one wavelength into said region of tissue of said body part at a surface of said body part and measuring light that is reflected, scattered, absorbed, or emitted by said region of tissue of said body part from an average sampling depth that is confined within said temperature controlled region of tissue of said body part, said average sampling depth not exceeding about 2 mm;
  (c) determining at least one optical property of said region of tissue of said body part at said temperature of step (a);
  (d) decreasing the temperature of said region of tissue of said body part to a temperature that is at least five degrees lower than the core temperature of said body part;
  (e) determining at least one optical property of said region of tissue of said body part at said decreased temperature of step (d);
  (f) increasing the temperature of said region of tissue of said body part to a temperature that is above the normal core temperature of said body part;
  (g) determining at least one optical property of said region of tissue of said body part at said increased temperature of step (f); and
  (h) analyzing the measurements of steps (c), (e), and (g) to obtain a measurement of said at least one parameter of said region of tissue of said body part, wherein said at least one parameter is the presence or concentration of glucose in said region of tissue of said body part.

31. The method of claim 30, wherein said parameter is the presence of a tissue heterogeneity that has thermal properties different from those of adjacent tissue.

32. The method of claim 30, wherein said parameter is the presence of a vascular change.

33. The method of claim 30, wherein the area of the body part subject to temperature control is at least two times the area of the body part being optically sampled.

34. The method of claim 30, wherein the area of the body part subject to temperature control is at least five times the area of the body part being optically sampled.

35. The method of claim 1, wherein said at least one wavelength is between 400 nm and 2500 nm, inclusive.

36. The method of claim 30, wherein said at least one optical parameter is reflectance.

37. The method of claim 30, wherein said at least one optical parameter is mean free path.

38. The method of claim 30, wherein said at least one optical parameter is effective attenuation coefficient.

39. The method of claim 30, wherein said at least one optical parameter is light penetration depth in tissue.

40. An apparatus for measuring concentration of glucose in a region of tissue of a body part comprising:
  (a) a temperature controlling element adapted to conform to the surface of said body part, said temperature controlling element capable of controlling the temperature of said region of tissue of said body part;
  (b) at least one light transmitting element and at least one light collecting element located within said temperature controlling element (a), said at lest one light transmitting element and said at lest one light collecting element positioned so that light that is measured is reflected, scattered, absorbed, or emitted by said region of tissue of said body part from an average sampling depth that is confined within said temperature controlled region of said body part, said average sampling depth not exceeding about 2 mm;
  (c) at least one light source for providing light to said at least one light transmitting element to illuminate said region of tissue of said body part subject to temperature control and at least one detector to measure intensity of light collected from said at least one light collecting element; and
  (d) a signal processor to determine an optical property of said region of tissue of said body part, said temperature controlling element capable of controlling the temperature of an area of the body part that is larger than the area of the body part being sampled by the at least one light source and at least one detector.

41. The apparatus of claim 40 where the distance of the at least one light transmitting element from the at least one light collecting element and the wavelengths of the source are selected to limit the depth of penetration in the tissue to that wherein the temperature is being controlled.

42. The apparatus of claim 41, wherein said at least one wavelength is between 400 nm and 2500 nm, inclusive.

43. The apparatus of claim 42, wherein said at least one wavelength is between 600 nm and 1300 nm, inclusive.

44. The apparatus of claim 42, wherein the separation distance between the center of said at least one light transmitting element and the center of said at least one light collecting element is no more than 6 mm.

* * * * *